(12) United States Patent
Ohiro et al.

(10) Patent No.: US 7,093,705 B2
(45) Date of Patent: Aug. 22, 2006

(54) ARTICLE TURNING-ROUND APPARATUS

(75) Inventors: Masaya Ohiro, Kagawa-ken (JP); Norikatsu Kushida, Kagawa-ken (JP); Hiroki Yamamoto, Kagawa-ken (JP)

(73) Assignee: Uni_Charm Corporation, Ehime-Ken (JP)

( * ) Notice: Subject to any disclaimer, the term of this patent is extended or adjusted under 35 U.S.C. 154(b) by 0 days.

(21) Appl. No.: 10/714,403

(22) Filed: Nov. 17, 2003

(65) Prior Publication Data

US 2004/0144620 A1    Jul. 29, 2004

(30) Foreign Application Priority Data

Nov. 18, 2002    (JP)    ............... 2002-333358

(51) Int. Cl.
*B65G 47/244* (2006.01)

(52) U.S. Cl. ............... 198/377.08; 198/374; 198/474.1; 198/471.1

(58) Field of Classification Search ............... 198/374, 198/377.08, 377.03, 377.04, 377.07, 474.1, 198/470.1, 471.1, 475.1
See application file for complete search history.

(56) References Cited

U.S. PATENT DOCUMENTS

| | | | | |
|---|---|---|---|---|
| 2,861,672 | A | * | 11/1958 | Buhrer et al. ............ 198/475.1 |
| 4,394,898 | A | * | 7/1983 | Campbell ............ 198/374 |
| 5,327,803 | A | * | 7/1994 | deMey, III ............ 198/475.1 |
| 5,417,037 | A | * | 5/1995 | Osti et al. ............ 198/374 |
| 5,988,354 | A | * | 11/1999 | Spatafora et al. ............ 198/374 |
| 6,604,623 | B1 | * | 8/2003 | Sumi et al. ............ 198/377.08 |

FOREIGN PATENT DOCUMENTS

| | | |
|---|---|---|
| EP | 0 895 951 | 2/1999 |
| EP | 1 048 595 | 11/2000 |
| JP | 8-310705 | 11/1996 |

* cited by examiner

*Primary Examiner*—Gene O. Crawford
*Assistant Examiner*—Mark A. Deuble
(74) *Attorney, Agent, or Firm*—Lowe Hauptman Berner, LLP

(57) ABSTRACT

An article turning-round apparatus includes a rotary table rotated by a first shaft, load-carrying tables mounted on the rotary table along a peripheral zone thereof, a first conveyor serving to convey articles to a first station and a second conveyor serving to convey the articles away from a second station. Each load-carrying table is either a first load-carrying table adapted to rotate counterclockwise or a second load-carrying table adapted to rotate clockwise around its own axis as it moves along with the peripheral zone of the rotary table. The articles are successively loaded, at the first station, on these load-carrying tables. The first load-carrying table is turned counterclockwise approximately by 90° and the second load-carrying table is turned clockwise approximately by 90° in the course of traveling from the first station to the second station.

6 Claims, 17 Drawing Sheets

ARTICLE TURNING-ROUND APPARATUS

BACKGROUND OF THE INVENTION

The present invention relates to an apparatus adapted to turn round a series of predetermined articles successively. The present application is based on, and claims priority from, Japanese Application Serial Number 2002-333358, filed Nov. 18, 2002, the disclosure of which is hereby incorporated by reference herein in its entirety.

Japanese Patent Application Publication No. 1996-310705A discloses a work turning-round apparatus proposed, which successively turns round a plurality of works fed at regular intervals by an angle of 90° relative to a direction in which the works are conveyed. These works are held on the apparatus in the course of being turned round.

The work turning-round apparatus disclosed in the above-cited Publication comprises a guide rail presenting a substantially oval profile, an endless conveyor circularly running along the guide rail, a plurality of carriages mounted on the endless conveyor and moving on the guide rail, table bases rotatably mounted on the carriages and work tables mounted on the table bases integrally therewith. The endless conveyor has a loading station and an unloading station for the sheet-like works and a pair of connecting conveyor sections extending between the loading station and the unloading station. In the case of this well-known work turning-round apparatus, rectilinear sections of the guide rail define the loading station and the unloading station, respectively, and curved sections of the guide rail define the connecting conveyor sections, respectively.

With this work turning-round apparatus, the works are held, at the loading station, on the respective work tables of the carriages and travel toward the unloading station through one of the connecting conveyor sections as the endless conveyor runs. Each of the table bases rotates by an angle of 90° relative to the associated carriage around its axis extending in a direction crossing the direction in which the works are conveyed and thereby turns round the work held on the work table by the corresponding angle. At the unloading station, this work is conveyed away from the turning-round apparatus. After the work has been conveyed away from the turning-round apparatus, the table base rotates again by an angle of 90° relative to the associated carriage, at the other of the connecting conveyor sections, around its axis crossing the direction in which the works are conveyed. In this way, each of the works rotates by an angle of 180° while the associated table base makes a circuit of the guide rail.

With the work turning-round apparatus disclosed in the above-cited Publication, the table bases can be rotated along the connecting conveyor sections but can be rotated neither at the loading station nor at the unloading station. This is for the reason that the guide rail rectilinearly extends at the loading and unloading stations and a plurality of the table bases closely lined up along these stations. If it is intended to rotate a pair of the adjacent table bases along the rectilinear sections of the guide rail defined by the loading and unloading stations, these table bases will bump against each other and prevented from smoothly rotating. Along the curved connecting conveyor sections, on the other hand, there is a difference in level between each pair of the adjacent table bases and therefore each of these adjacent table bases can be rotated without any interference with each other.

This work turning-round apparatus is constructed so that the table bases rotate around their own axes along the curved sections of the guide rail (i.e., connecting conveyor sections) and loading as well as unloading of the works is carried out along the rectilinear sections of the guide rail (i.e., the loading station and the unloading station). Thus a restriction is imposed on the positions on the apparatus at which the works are loaded and are unloaded.

In this work turning-round apparatus, the carriages travel on the guide rail by means of guide rollers mounted on these carriages and a plurality of the table bases rotate on their own axes while these table bases travel on the guide rail. Such construction not complicates the structure of the apparatus but also is unsuitable for the purpose of turning round the works at a high velocity.

SUMMARY OF THE INVENTION

It is an object of the present invention to provide an article turning-round apparatus improved so that a series of the articles can be successively turned round at a high velocity and there is no restriction imposed on the positions at which the articles are loaded and unloaded.

According to the present invention, there is provided an article turning-round apparatus provided with first and second stations at which a plurality of disposable wearing articles each having, in addition to front and rear waist regions opposed to each other, a waist-surrounding upper end zone and a crotch bottom zone, are successively loaded and unloaded, respectively, and adapted to successively turn round the articles moving from the first station to the second station.

The improvement according to the present invention is characterized by that the turning-round apparatus further comprises a rotary base adapted to be rotated by means of a first shaft and provided along a peripheral zone thereof with the first and second stations and a plurality of load-carrying tables arranged at regular intervals along the peripheral zone, the load-carrying tables being adapted to carry thereon the articles of which said front or rear waist regions are held in contact with the load-carrying tables; the load-carrying tables comprise first load-carrying tables rotatably mounted on the rotary base by means of second shafts extending in an axial direction of the first shaft so as to be rotated around their own axes in the peripheral zone of the rotary base and to be simultaneously moved along with the peripheral zone of the rotary base as the rotary base rotates and second load-carrying tables rotatably mounted on the rotary base by means of third shafts extending in the axial direction of the first shaft so as to be rotated around their own axes in the peripheral zone of the rotary base and to be simultaneously moved along with the peripheral zone of the rotary base as the rotary base rotates wherein the first and second load-carrying tables are alternately arranged on the rotary base so that each of the second load-carrying tables be interposed between each pair of the first load-carrying tables; and the first and second load-carrying tables are successively loaded with the articles having respective waist-surrounding upper end zones lined up in a predetermined direction as soon as the first and second load-carrying tables alternately reach the first station as the rotary base rotates wherein the first load-carrying tables are rotated around their own axes in the peripheral zone of the rotary base and thereby turned round approximately by an angle of 90° clockwise or counterclockwise while the first load-carrying tables move from the first station to the second station and the second load-carrying tables are rotated around their own axes in the peripheral zone of the rotary base and thereby turned round approximately by an angle of 90° in the direction opposite to that of the first load-carrying tables while the second load-carrying tables move from the first station to the second station as the rotary base rotates.

The present invention includes the following embodiments.

The first and second load-carrying tables include a first suction mechanism functioning to hold the articles on the first and second load-carrying tables under a suction effect so that the first and second load-carrying tables move along with the peripheral zone of the rotary base from the first station to the second station together with the articles held thereon under the suction effect and simultaneously rotate around their own axes in the peripheral zone of the rotary base.

The article turning-round apparatus further comprises a first conveyor belt assembly adapted to convey the articles at regular intervals to the first station of the rotary base so that each pair of adjacent the articles may have respective waist-surrounding upper end zones lined up with each other and a second conveyor belt assembly adapted to convey the articles away from the second station of the rotary base at regular intervals so that each pair of the adjacent articles may have respective waist-surrounding upper end zones opposed to each other.

The article turning-round apparatus further comprises a first conveyor belt assembly adapted to convey the articles at regular intervals to the first station of the rotary base so that each pair of adjacent the articles may have respective waist-surrounding upper end zones and respective crotch bottom zones opposed to each other and a second conveyor belt assembly adapted to convey the articles away from the second station of the rotary base at regular intervals so that each pair of adjacent the articles may have respective waist-surrounding upper end zones and respective crotch bottom zones lined up each other.

The first conveyor belt assembly includes a second suction mechanism adapted to hold said articles on the first conveyor belt under a suction effect and, when the first and second load-carrying tables come face to face with the first conveyor belt assembly, the first suction mechanism effectively functions against the effect of the second suction mechanism to transfer the articles from the first conveyor belt assembly onto the first and second load-carrying tables.

The second conveyor belt assembly includes a third suction mechanism adapted to hold the articles on the second conveyor belt under a suction effect and, when the first and second load-carrying tables come face to face with the second conveyor belt assembly, the third suction mechanism effectively functions against the effect of the first suction mechanism to transfer the articles from the first and second load-carrying tables onto the second conveyor belt assembly.

The article is a pull-on disposable diaper comprising a liquid-pervious topsheet facing a wearer's body, a liquid-impervious backsheet facing away from the wearer's body and a liquid-absorbent core interposed between the top- and backsheets and formed with a waist-hole and a pair of leg-holes.

DETAILED DESCRIPTION OF THE PREFERRED EMBODIMENTS

Details of a article turning-round apparatus according to the present invention will be more fully understood from the description predetermined hereunder with reference to the accompanying drawings.

Figure 1:
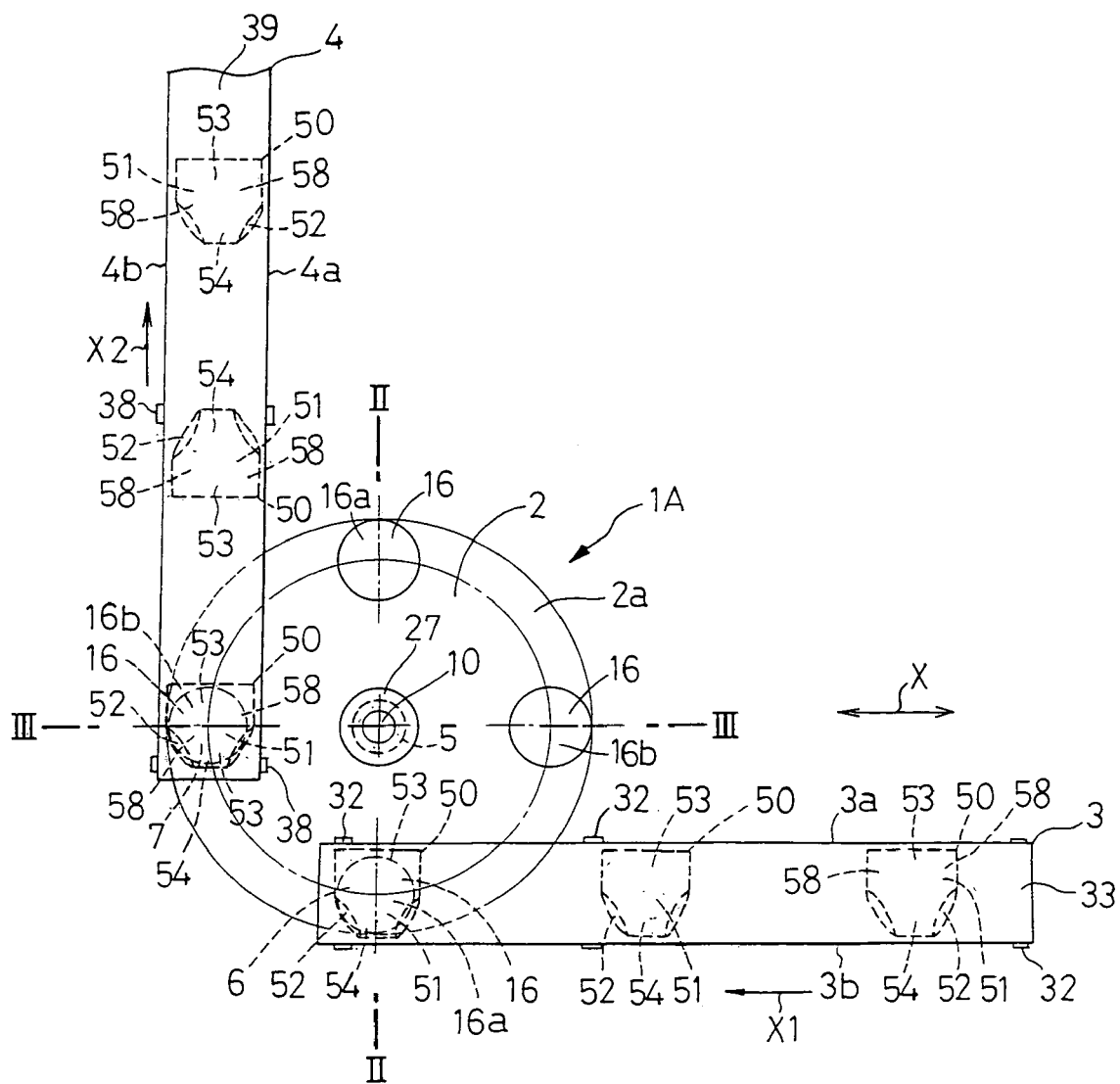
FIG. 1 is a top view showing an article turning-round apparatus having timing belts not shown.
Figure 2:
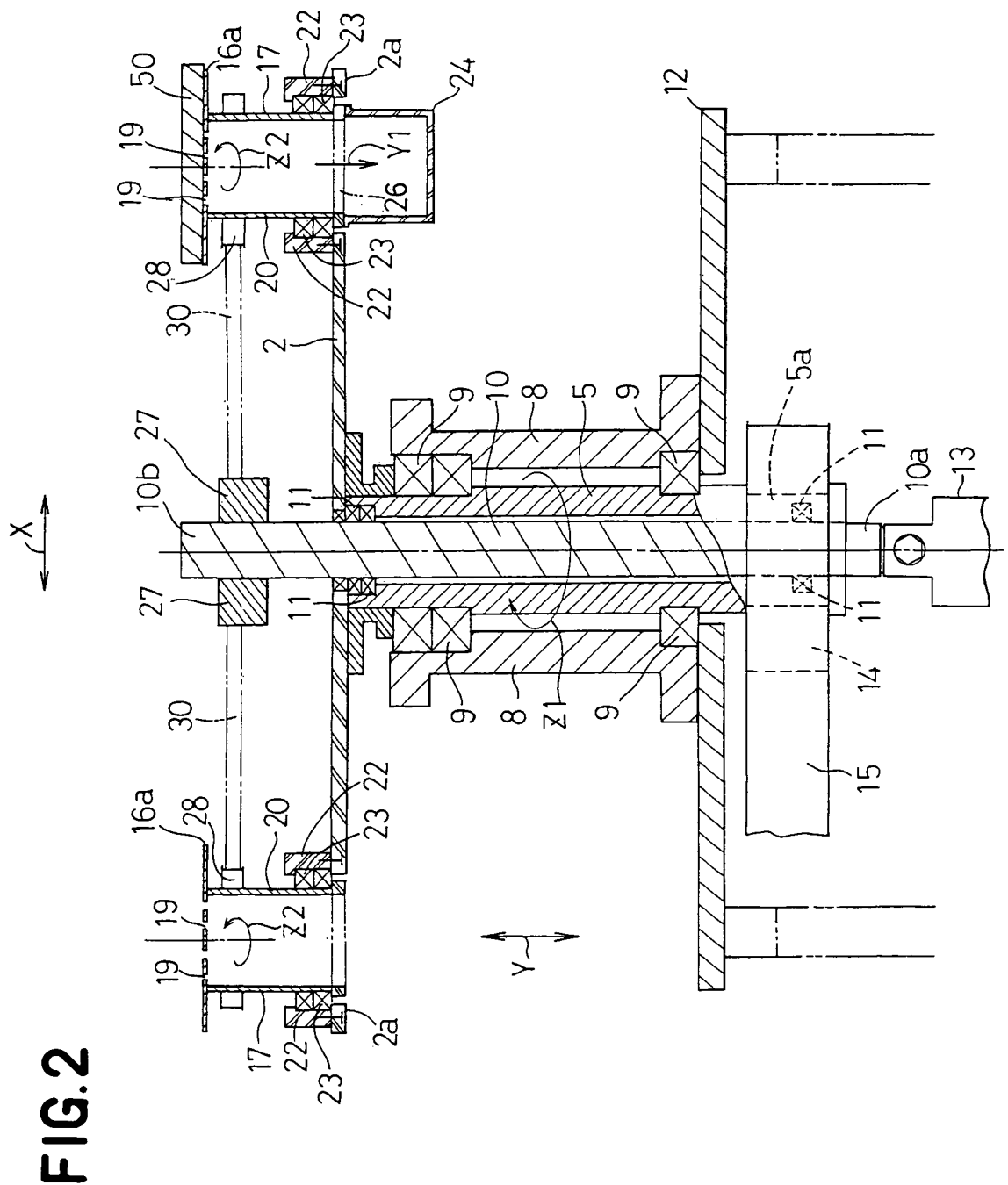
FIG. 2 is a sectional view taken along a line II—II in FIG. 1.
Figure 3:
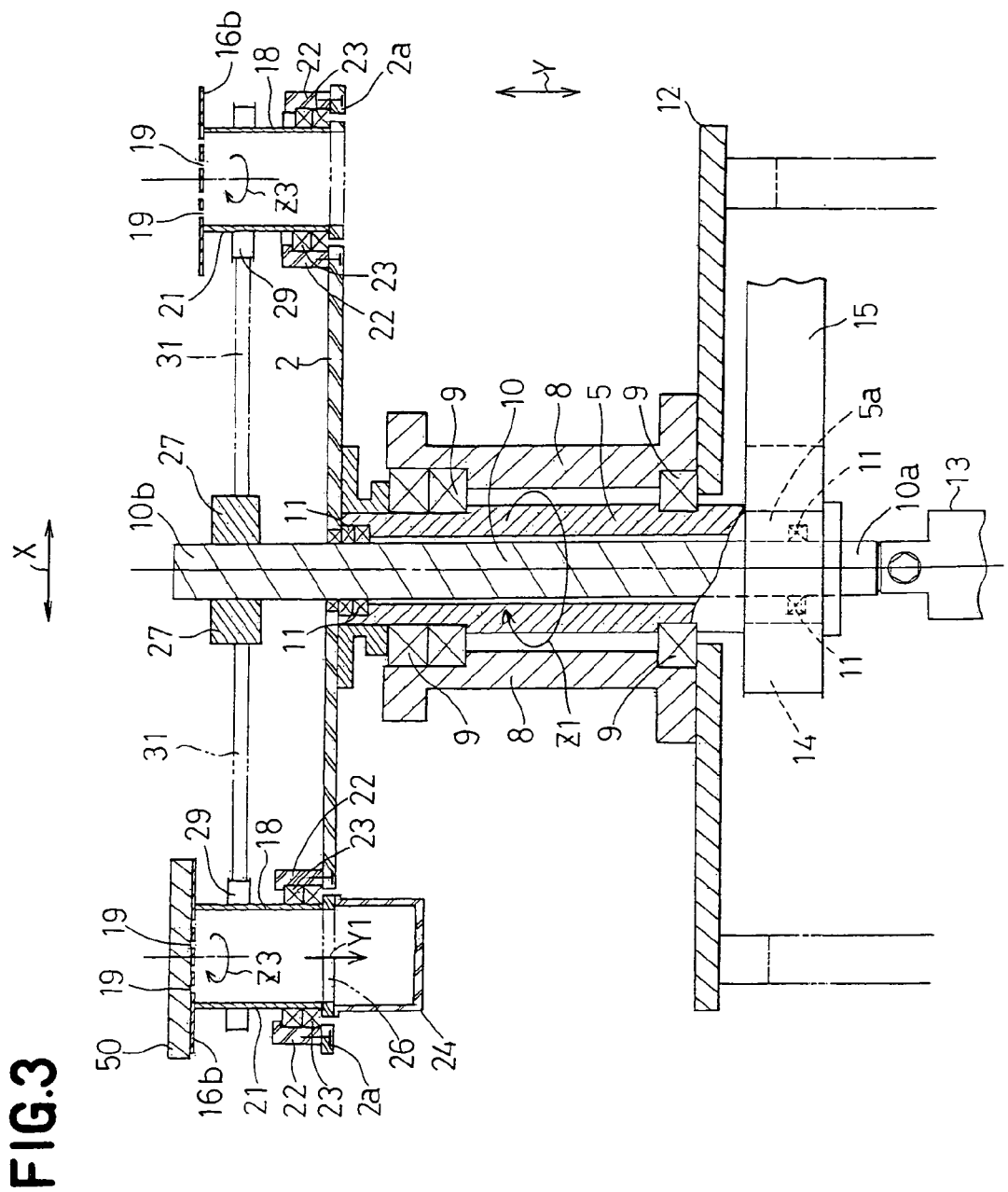
FIG. 3 is a sectional view taken along a line III—III in FIG. 1.

FIG. 1 is a top view showing an article turning-round apparatus 1A having timing belts 30, 31 not shown, FIG. 2 is a sectional view taken along a line II—II in FIG. 1 and FIG. 3 is a sectional view taken along a line III—III in FIG. 1 with first and second conveyor belt assemblies 3, 4 not shown. In FIGS. 1 through 3, a vertical direction is indicated by an arrow Y and a horizontal direction is indicated by an arrow X.

The turning-round apparatus 1A functions to turn round a plurality of disposable diapers 50 (disposable wearing article) continuously manufactured and fed at regular intervals. The turning-round apparatus 1A comprises a rotary table 2 (rotary base) provided with a plurality of load-carrying tables 16 mounted thereon, a first conveyor belt assembly 3 serving to convey the diapers 50 onto the rotary table 2 and a second conveyor belt assembly 4 serving to convey the diapers 50 away from the rotary table 2.

The rotary table 2 has a first tubular shaft 5 extending in the vertical direction around which the rotary table 2 is rotated. A peripheral zone 2a of the rotary table 2 is provided with the first station 6 at which the diapers 50 are loaded from the first conveyor belt assembly 3 onto the rotary table 2 and the second station 7 at which the diapers 50 are unloaded from the rotary table 2 onto the second conveyor belt assembly 4. The second station 7 corresponds to a position along the peripheral zone 2a of the rotary table 2 at which the rotary table 2 has been rotated by an angle of 90° from the first station 6 (i.e., the second station 7 is located at an angular distance of 90° from the first station 6). There is provided externally of the rotary table 2 an electric motor (not shown) rotationally driving the first shaft 5.

A part of the first shaft 5 extending downward from the rotary table 2 is covered with a tubular stationary frame 8 and bearings 9 are interposed between these first shaft 5 and tubular stationary frame 8. Within the first shaft 5, a stationary shaft 10 extends with bearings 11 interposed therebetween. The stationary frame 8 is fixed to a pedestal 12. The first shaft 5 and the stationary shaft 10 rise above the pedestal 12. The bearings 9 are interposed between the outer peripheral surface of the first shaft 5 and the inner peripheral surface of the stationary frame 8 and the bearings 11 are interposed between the inner peripheral surface of the first shaft 5 and the outer peripheral surface of the stationary shaft 10. The first shaft 5 rotates between the stationary frame 8 and the stationary shaft 10. The stationary shaft 10 has its lower end 10a connected to a lock member 13 and therefore can not be rotated. The first shaft 5 is provided on its lower end 5a with a pulley 14. Rotation of the electric motor is transmitted by a drive belt 15 passed on the pulley 14 to the first shaft 5. Rotation of the first shaft 5 causes the rotary table 2 to rotate in the same direction as the direction in which the first shaft 5 rotates.

The load-carrying tables 16 are mounted on the upper surface of the rotary table 2 along the peripheral zone 2a at regular intervals in the circumferential direction. The load-carrying tables 16 comprise first load-carrying tables 16a mounted on the rotary table 2 so as to be rotatable around second shafts 17 extending in the vertical direction (i.e., in an axial direction of the first shaft 5) and second load-carrying tables 16b mounted on the rotary table 2 so as to be rotatable around third shafts 18 extending in the vertical direction (i.e., in the axial direction of the first shaft 5). These first and second load-carrying tables 16a, 16b are alternately arranged along the peripheral zone 2a of the rotary table 2 so that each of the second load-carrying tables 16b is interposed between each pair of the adjacent first load-carrying tables 16a, 16a.

Each of these first and second load-carrying tables 16a, 16b has a first suction mechanism serving to hold the diaper 50 under a suction effect and formed with a plurality of openings extending through the first and second load-carrying tables 16a, 16b between their upper and lower surfaces. The first and second load-carrying tables 16a, 16b are provided with cylindrical ducts 20, 21 extending downward from these first and second load-carrying tables 16a, 16b, respectively.

The ducts 20 of the first load-carrying tables 16a are supported by support members 22 mounted on the rotary table 2 by means of bearings 23. The ducts 20 define the second shafts 17 associated with the first load-carrying tables 16a and rotate together with the first load-carrying tables 16a. The ducts 21 associated with the second load-carrying tables 16b are supported by the support members 22 mounted on the rotary table 2 by means of the bearings 23. The ducts 21 define the third shafts 18 associated with the second load-carrying tables 16b and rotate together with the second load-carrying tables 16b.

A suction box 24 underlies the rotary table 2. The suction box 24 is provided with a duct 25 (See FIGS. 4 and 5). The suction box 24 extends along the peripheral zone 2a of the rotary table 2 from the first station 6 to the second station 7. The suction box 24 is provided on its top with an opening 26. The rotary table 2 overlies the opening 26. In the suction box 24, an air is constantly sucked through the duct 25.

In the first suction mechanism, rotation of a fan (not shown) causes an air to be sucked through the ducts 20, 21 vertically downward as indicated by an arrow Y1 in FIGS. 2, 3 so that a pressure within the ducts 20, 21 may be maintained at a negative pressure (an air pressure approximates vacuum). Specifically, an air is sucked through the openings 19 of the first and second load-carrying tables 16a, 16b into the respective ducts 20, 21 and flows from the suction box 24 toward the ducts 25 as the fan rotates. Consequently, a sucking force is generated so as to be exerted on the first and second load-carrying tables 16a, 16b from upper surfaces toward lower surfaces thereof.

An upper end 10b of the stationary shaft 10 is provided thereon with a belt-holding portion 27. The second shafts 17 (i.e., the ducts 20) of the second load-carrying tables 16b are provided thereon with pulleys 28, 29. A timing belt 30 is passed on elements 27, 28. Rotation of the rotary table 2 causes the first load-carrying tables 16a to move along with the peripheral zone 2a of the rotary table 2 and the belt 30 to travel along the periphery of the belt-holding portion 27. Thus a turning force is transmitted by the belt 30 to the pulley 28 and thereby the first load-carrying tables 16a rotate around their own axes by means of the second shafts 17 (i.e., by means of the ducts 20) in the peripheral zone 2a of the rotary table 2. A timing belt 31 is passed on elements 27 and 29. Rotation of the rotary table 2 causes the second load-carrying tables 16b to move along with the peripheral zone 2a of the rotary table 2 and simultaneously causes the belt 31 to travel along the periphery of the belt-holding portion 27. Thus a turning force is transmitted by the belt 31 to the pulley 29 and thereby the second load-carrying tables 16b rotate around their own axes by means of the third shafts 18 (i.e., by means of the ducts 21) in the peripheral zone 2a of the rotary table 2.

In the case of this turning-round apparatus 1A, a pair of the first load-carrying tables 16a and a pair of the second load-carrying tables 16b are mounted on the rotary table 2. A line segment extending from the central point of the first shaft 5 to the central point of the first load-carrying table 16a and a line section extending from the central point of the first shaft 5 to the central point of the second load-carrying table 16b include an angle of 90° therebetween, so these load-carrying tables 16a, 16b are located along the peripheral zone 2a of the rotary table 2 at the angular intervals of 90°. It should be noted here that the total number of these load-carrying tables 16a, 16b are not limited to four as illustrated so far as the number of the first load-carrying tables 16a and the number of the second load-carrying tables 16b are respectively plural and equal to each other.

If three first load-carrying tables 16a and three second load-carrying tables 16b are mounted on the rotary table 2, the line segment extending from the central point of the first shaft 5 to the central point of the first load-carrying table 16a and the line section extending from the central point of the first shaft 5 to the central point of the second load-carrying table 16b will include an angle of 60° therebetween, so these load-carrying tables 16a, 16b will be located along the peripheral zone 2a of the rotary table 2 at the angular intervals of 60°. If four first load-carrying tables 16a and four second load-carrying tables 16b are mounted on the rotary table 2, the line segment extending from the central point of the first shaft 5 to the central point of the first load-carrying table 16a and the line section extending from the central point of the first shaft 5 to the central point of the second load-carrying table 16b will include an angle of 45° therebetween, so these load-carrying tables 16a, 16b will be located along the peripheral zone 2a of the rotary table 2 at the angular intervals of 45°.

Figure 4:
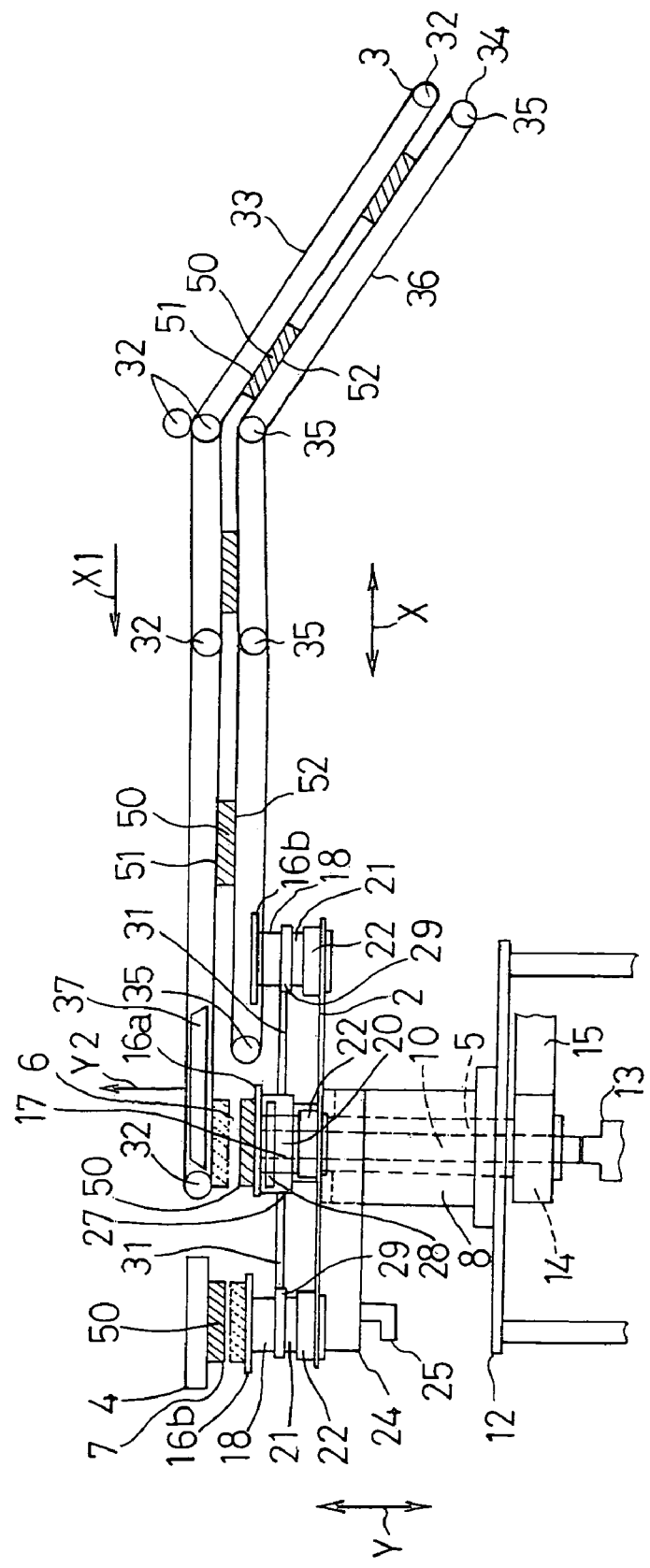
FIG. 4 is a side view showing the turning-round apparatus as viewed from the side of a first station.
Figure 5:
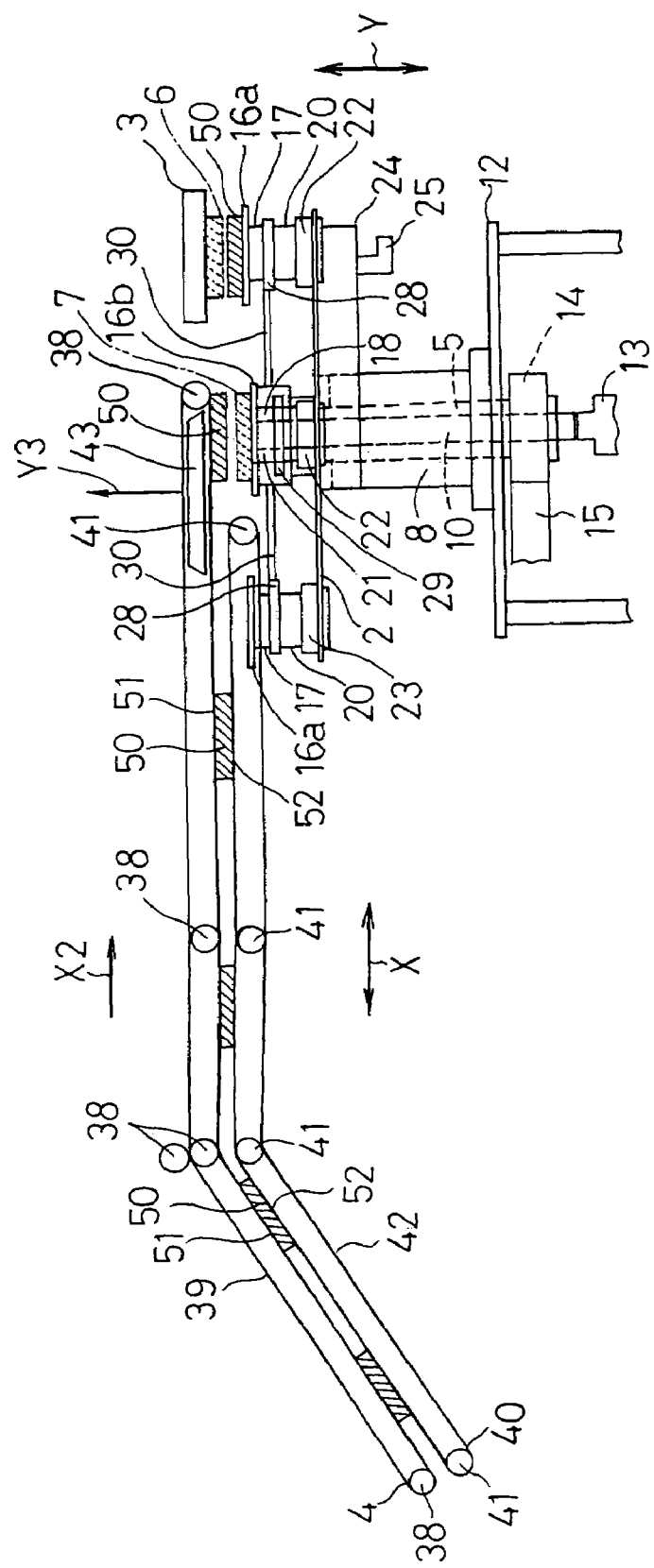
FIG. 5 is a side view showing the turning-round apparatus as viewed from the side of a second station.

FIG. 4 is a side view showing the turning-round apparatus 1A as viewed from the side of a first station 6 and FIG. 5 is a side view showing the turning-round apparatus 1A as viewed from the side of a second station 7. In FIGS. 4 and 5, a vertical direction is indicated by an arrow Y and a horizontal direction is indicated by an arrow X.

As will be seen in FIG. 4, the first conveyor belt assembly 3 comprises a plurality of belt pulleys 32 and a belt 33 passed on these belt pulleys 32. The belt 33 circularly runs as the belt pulleys 32 rotate. Below the first conveyor belt assembly 3, a third conveyor belt assembly 34 is located. The third conveyor belt assembly 34 comprises a plurality of belt pulleys 35 and a belt 36 passed on these belt pulleys 35. The belt 36 circularly runs in synchronization with the belt 33 as the belt pulleys 35 rotate. The first conveyor belt assembly 3 extends in the horizontal direction toward the peripheral zone 2a of the rotary table 2 so as to reach the first station 6 on the upper surface of the rotary table 2. The third conveyor belt assembly 34 extends in the horizontal direction toward the peripheral zone 2a of the rotary table 2 so as to terminate short of the peripheral zone 2a of the rotary table 2.

The first conveyor belt assembly 3 is provided with a second suction mechanism serving to suck the diapers 50 and thereby to hold them. The belt 33 of the first conveyor belt assembly 3 is formed with a plurality of openings (not shown) extending through the belt 33 between its upper and lower surfaces. A suction box 37 is interposed between upper and lower pathways of the belt 33. This suction box 37 extends from the vicinity of the first station 6 above this first station 6. The suction box 37 is formed with a plurality openings (not shown) extending through its lower surface.

In the second suction mechanisms, rotation of a fan (not shown) causes an air to be sucked into the suction box 37 in a direction indicated by an arrow Y2 in FIG. 4. Specifically, the air flows through the openings of the belt 33 from the outer surface to the inner surface of the belt 33 and then into the suction box 37 through the openings of the suction box 37 as the fan rotates. Consequently, a sucking force is generated so as to be exerted on the belt 33 from its outer surface toward its inner surface.

The diapers 50 are held between the first conveyor belt assembly 3 and the third conveyor belt assembly 34 and conveyed by these conveyor belt assemblies 3, 34 at the regular intervals toward the first station 6 of the rotary table 2 as indicated by the arrow X1 in FIGS. 1 and 4. These diapers 50 have their front waist regions 51 held in contact with the first conveyor belt assembly 3, the rear waist regions 52 held in contact with the third conveyor belt assembly 34, the waist-surrounding upper end zones 53 lying on the side of the inner side edge 3a of the conveyor belt assembly 3 and the crotch bottom zones 54 lying on the side of the outer edge 3b of the conveyor belt assembly 3. Along the first and third conveyor belt assemblies 3, 34, the waist-surrounding upper end zones 53 of these diapers 50 line up in a direction in which these diapers 50 are conveyed (i.e., in the direction X1) and the crotch bottom zones 54 of these diapers 50 also line up in this direction (i.e., in the direction X1). The diapers 50 are successively held on the first conveyor belt assembly 3 under the effect of the second suction mechanism as the diapers 50 get nearer to the first station 6.

It should be understood that the third conveyor belt assembly 34 may be eliminated from this turning-round apparatus 1A. In this case, the suction box 37 interposed between the upper and lower pathways of the belt 33 will cover a substantially entire area of the first conveyor belt assembly 3 so that the diapers 50 can be reliably held by the first conveyor belt assembly 3 under the suction effect until these diapers 50 successively reach the first station 6.

As will be seen in FIG. 5, the second conveyor belt assembly 4 comprises a plurality of belt pulleys 38 and a belt 39 passed on these belt pulleys 38. The belt 39 circularly runs as the belt pulleys 38 rotate. Below the second conveyor belt assembly 4, a fourth conveyor belt assembly 40 is located. The fourth conveyor belt assembly 40 comprises a plurality of belt pulleys 41 and a belt 42 passed on these belt pulleys 41. The belt 42 circularly runs in synchronization with the belt 39 as the belt pulleys 41 rotate. The second conveyor belt assembly 4 extends in the horizontal direction toward the peripheral zone 2a of the rotary table 2 so as to reach the second station 7 on the upper surface of the rotary table 2. The fourth conveyor belt assembly 40 extends in the horizontal direction toward the peripheral zone 2a of the rotary table 2 so as to terminate short of the peripheral zone 2a of the rotary table 2.

The second conveyor belt assembly 4 is provided with a third suction mechanism serving to suck the diapers 50 and thereby to hold them. The belt 39 of the second conveyor belt assembly 4 is formed with a plurality of openings (not shown) extending through the belt 39 between its upper and lower surfaces. A suction box 43 is interposed between upper and lower pathways of the belt 39. This suction box 43 extends from the vicinity of the second station 7 above this second station 7. The suction box 43 is formed with a plurality openings (not shown) extending through its lower surface.

In the third suction mechanisms, rotation of a fan (not shown) causes the air to be sucked into the suction box 43 in a direction indicated by an arrow Y3 in FIG. 5. Specifically, the air flows through the openings of the belt 39 from the outer surface to the inner surface of the belt 39 and then into the suction box 43 through the openings of the suction box 43. Consequently, a sucking force is generated so as to be exerted on the belt 39 from its outer surface toward its inner surface.

The diapers 50 are held on the second conveyor belt assembly 4 under the effect of the third suction mechanism associated with this second conveyor belt assembly 4, then held between the second conveyor belt assembly 4 and the fourth conveyor belt assembly 40 and conveyed by these conveyor belt assemblies 4, 40 at the regular intervals away from the rotary table 2 as indicated by the arrow X2 in FIGS. 1 and 5. These diapers 50 have their front waist regions 51 held in contact with the second conveyor belt assembly 4 and the rear waist regions 52 held in contact with the fourth conveyor belt assembly 40. On the second conveyor belt assembly 4, the front waist regions 51 of each pair of the adjacent diapers 50 are opposed to each other, the crotch bottom zones 54 of each pair of the adjacent diapers 50 are opposed to each other and the transversely opposite waist lateral zones 58 of the diaper 50 extend parallel to the inner and outer side edges 4a, 4b of the conveyor belt assembly 4.

It should be understood that the fourth conveyor belt assembly 40 may be eliminated from this turning-round apparatus 1A. In this case, the suction box 43 interposed between the upper and lower pathways of the belt 39 will cover a substantially entire area of the second conveyor belt assembly 4 so that the diapers 50 can be reliably held on the second conveyor belt assembly 4 under the suction effect until these diapers 50 are successively conveyed away from the rotary table 2 at the second station 7.

Figure 6:
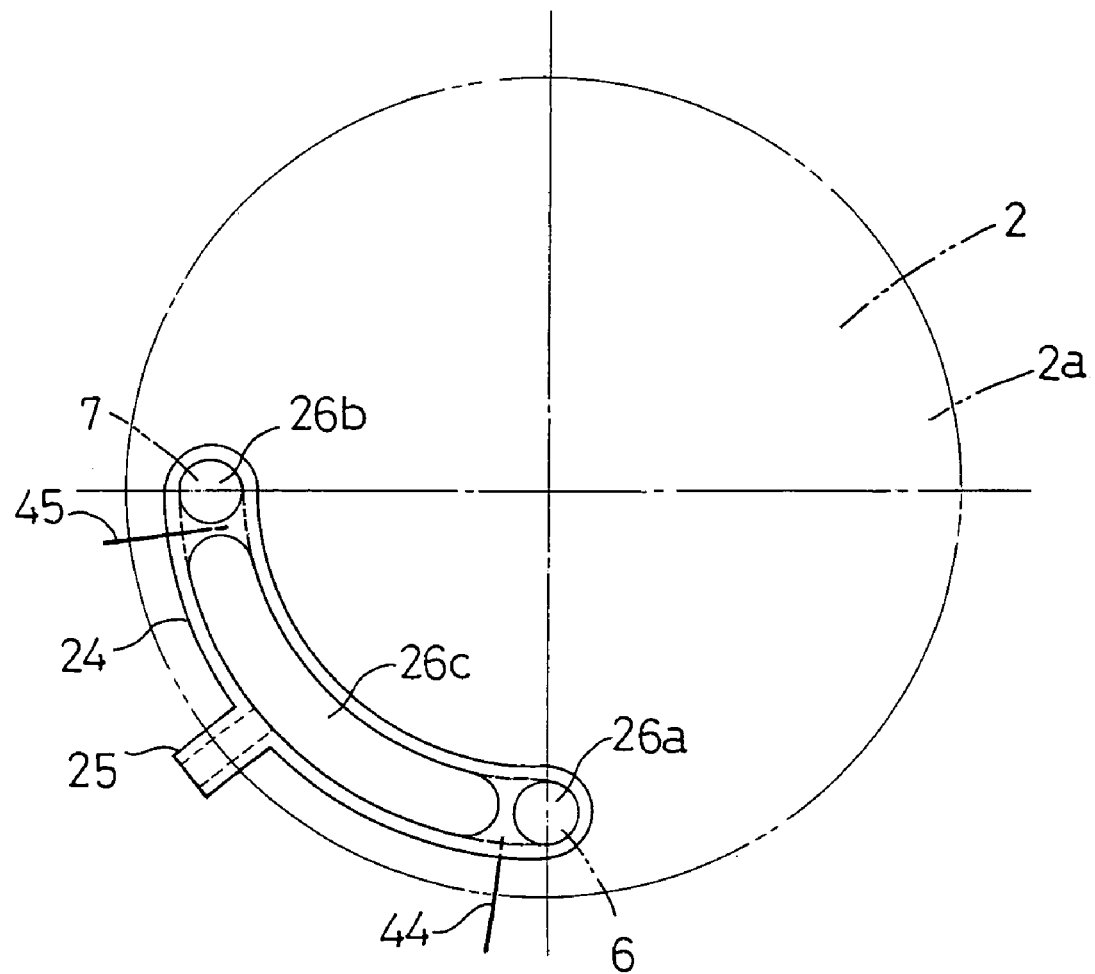
FIG. 6 is a top view showing a suction box.
Figure 7:
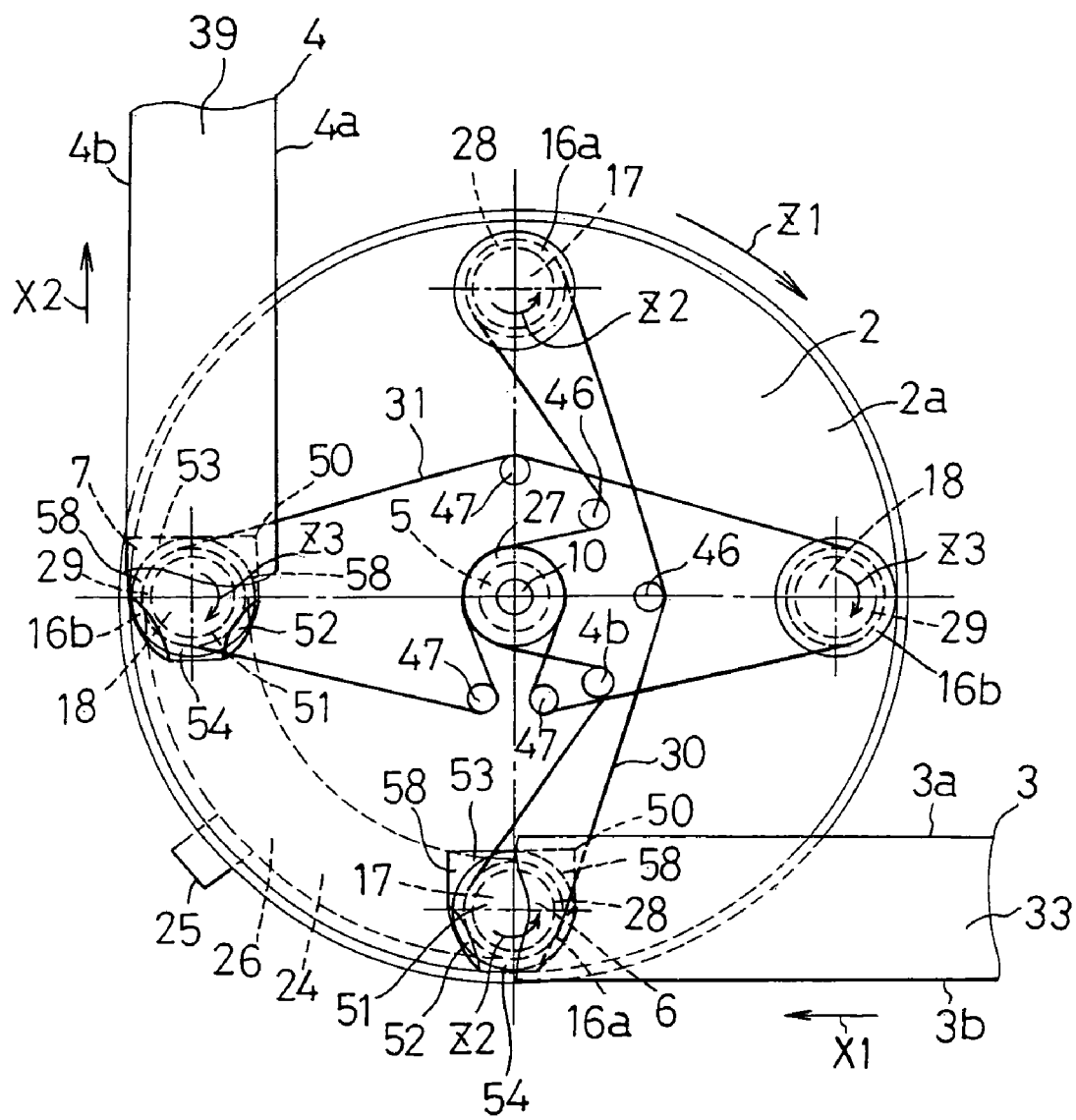
FIG. 7 is a partially cutaway scale-enlarged top view showing the article turning-round apparatus with first and second conveyor belt assemblies.
Figure 8:
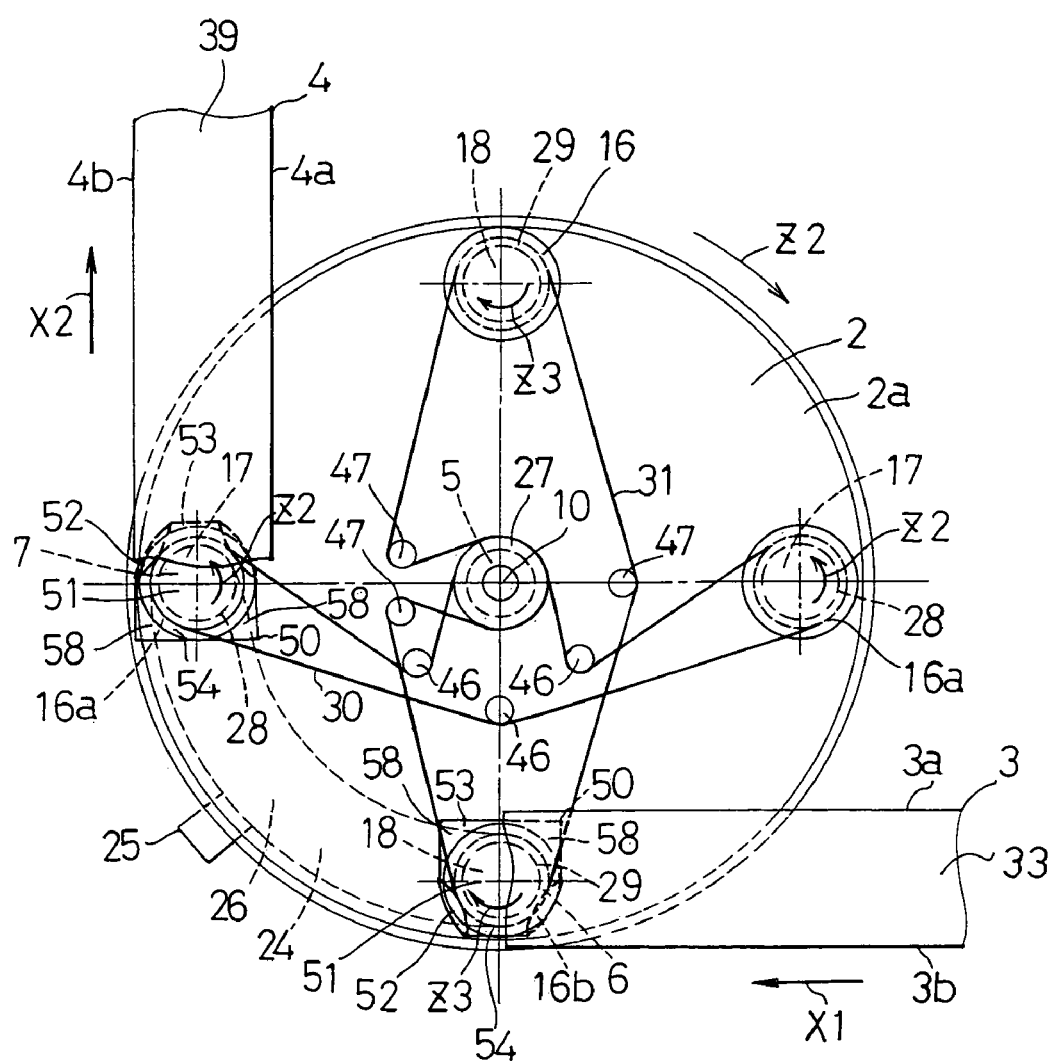
FIG. 8 is a partially cutaway scale-enlarged top view showing the article turning-round apparatus with first and second conveyor belt assemblies.
Figure 9:
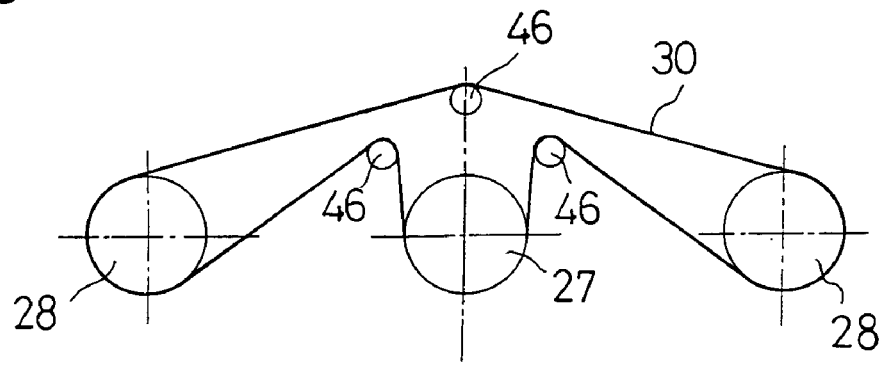
FIG. 9 is a diagram schematically illustrating a belt passed on pulleys associated with stationary shafts and pulleys associated with first load-carrying tables.
Figure 10:
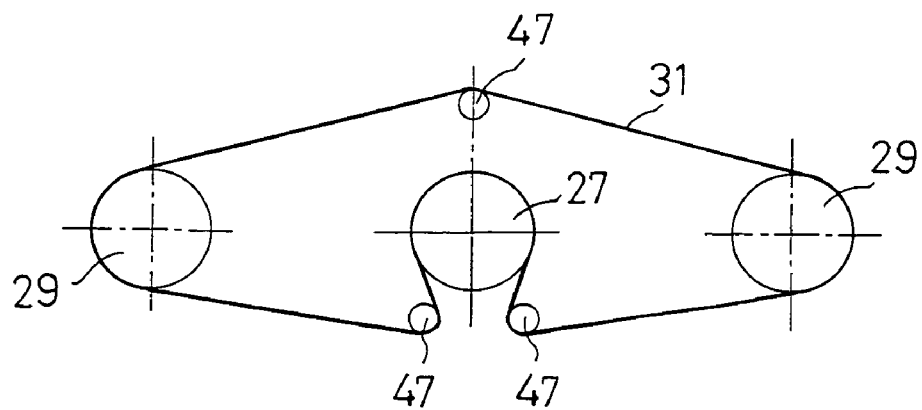
FIG. 10 is a diagram schematically illustrating a belt passed on the pulleys associated with the stationary shafts and pulleys association with second load-carrying tables.

FIG. 6 is a top view showing a suction box 24, FIGS. 7 and 8 are partially cutaway scale-enlarged top views showing the turning round apparatus 1A with the first and second conveyor belt assemblies 3, 4, FIG. 9 is a diagram schematically illustrating a belt 30 passed on belt-holding portion 27 of the stationary shaft 10 and pulleys 28 associated with first load-carrying tables 16a and FIG. 10 is a diagram schematically illustrating a belt 31 passed on the belt-holding portion 27 of the stationary shaft 10 and pulleys 29 association with second load-carrying tables 16b. In FIG. 6, the rotary table 2 is indicated by chain double-dashed line. In FIGS. 7 and 8, the suction boxes 37, 43 are not shown. In FIG. 7, the first load-carrying tables 16a have reached the first station 6 on the rotary table 2 and the second load-carrying tables 16b have reached the second station 7 on the rotary table 2. In FIG. 8, the second load-carrying tables 16b have reached the first station 6 on the rotary table 2 and the first load-carrying tables 16a have reached the second station 7.

The opening 26 of the suction box 24 comprises a first opening 26a located at the first station 6, a second opening 26b located at the second station 7 and a third opening 26c extending between these first and second openings 26a, 26b. While these openings 26a, 26b, 26c of the suction box 24 are substantially closed by the rotary table 2, a slight clearance is defined between each pair of the adjacent openings 26a, 26b, 26c. A partition plate 44 is inserted between the openings 26a, 26c and a partition plate 45 is inserted between the openings 26b, 26c.

An inner cross-sectional area of the suction box 24 is adjusted by these partition plates 44, 45. The inner cross-sectional area of the suction box 24 is adjustably reduced by these partition plates 44, 45 to reduce a suction force (air suction capacity) at these openings 26a, 26b and the inner cross-sectional area of the suction box 24 is adjustably enlarged by these partition plates 44, 45 to enhance the suction force (air suction capacity) at these openings 26a, 26b.

Between the opening 26a and the opening 26c, the inner cross-sectional area of the suction box 24 is enlarged and thereby the suction force at the opening 26a is enhanced. Between the opening 26b and the opening 26c, the inner cross-sectional area of the suction box 24 is reduced and thereby the suction force at the opening 26b is correspondingly reduced.

The belt-holding portion 27 mounted on the stationary shaft 10 and the pulleys 28 mounted on the respective second shafts 17 (the ducts 20) of the first load-carrying tables 16a have an effective radius ratio (a rotational velocity ratio) of 1:1. As illustrated in FIG. 9, the timing belt 30 is passed on the belt-holding portion 27 and the pulleys 28 in open-fashion as illustrated in FIG. 9. Between the belt-holding portion 27 and the respective pulleys 28, there are provided guide wheels 46 serving to maintain a desired tension of the belt 30.

The belt-holding portion 27 mounted on the stationary shaft 10 and the pulleys 29 mounted on the respective third shafts 18 (the ducts 21) of the second load-carrying tables 16b have an effective radius ratio (a rotational velocity ratio) of 1:1. As illustrated in FIG. 10, the timing belt 31 is passed on the belt-holding portion 27 and the pulleys 29 in a cross-fashion. Between the belt-holding portion 27 and the respective pulleys 29, there are provided guide wheels 47 serving to maintain a desired tension of the belt 31. A rotational velocity ratio among elements 27, 28, 29 depends on an effective radius ratio of elements 27, 28, 29.

In this turning-round apparatus 1A, movement of the first load-carrying tables 16a approximately by an angle of 90° clockwise (i.e., in the direction Z1) along with the peripheral zone 2a of the rotary table 2 from the first station 6 toward the second station 7 causes a turning force to be transmitted from the belt 30 to the pulleys 28 and thereby causes the first load-carrying tables 16a to rotate together with the respective ducts 20 counterclockwise (i.e., in the direction Z2) around their own axes approximately by an angle of 90° in the peripheral zone 2a of the rotary table 2. Movement of the second load-carrying tables 16b approximately by an angle of 90° clockwise (i.e., in the direction Z1) along with the peripheral zone 2a of the rotary table 2 from the first station 6 toward the second station 7 causes a turning force to be transmitted from the belt 31 to the pulleys 29 and thereby causes the second load-carrying tables 16b to rotate together with the respective ducts 21 clockwise (i.e., in the direction Z3) around their own axes approximately by an angle of 90° in the peripheral zone 2a of the rotary table 2.

Now operation of this turning-round apparatus 1A will be described more in details. In parallel with conveyance of the diapers 50 toward the first station 6 by means of the first and third conveyor belt assemblies 3, 34, the rotary table 2 rotates clockwise (i.e., in the direction Z1) so that any one of the first load-carrying tables 16a or the second load-carrying tables 16b reaches the first station 6. Thereupon the ducts 20, 21 come just above the first opening 26a of the suction box 24 to establish a communication between the ducts 20, 21 and the opening 26a. As a result, the air is sucked through the openings 19 of the first and second load-carrying tables 16a, 16b into the ducts 20, 21 and thereby the first suction mechanism associated with the load-carrying tables 16a, 16b is actuated.

The respective diapers 50 are transferred from the first conveyor belt assembly 3 onto the load-carrying tables 16a, 16b under the suction effect. The diapers 50 have the respective rear waist regions 52 kept in contact with the upper surfaces of these load-carrying tables 16a, 16b under the suction effect. The first and second load-carrying tables 16a, 16b alternately reach the first station 6 and the diapers 50 are successively transferred onto these load-carrying tables 16a, 16b as the rotary table 2 rotates. At the first station 6, these diapers 50 are carried by the first and second load-carrying tables 16a, 16b with the waist-surrounding upper end zones 53 of these diapers 50 being lined up in a predetermined direction.

In this turning-round apparatus 1A, a suction force of the suction box 24 is previously adjusted to be higher than a suction force of the suction box 37 so that the first suction mechanism can effectively function against the function of the second suction mechanism. Consequently, the first suction mechanism effectively functions against the second suction mechanism and thereby allows the diapers 50 to be quickly transferred from the conveyor belt assembly 3 onto the load-carrying tables 16a, 16b at the first station 6.

The first load-carrying tables 16a and the second load-carrying tables 16b carrying the diapers 50 thereon, respectively, move along with the peripheral zone 2a of the rotary table 2 from the first station 6 toward the second station 7 of the rotary table 2. The first load-carrying tables 16a counterclockwise rotate on their own axes in the peripheral zone 2a of the rotary table 2 approximately by an angle of 90°. Correspondingly, the diapers 50 held on the first load-carrying tables 16a are counterclockwise turned round approximately by an angle of 90° in the course of traveling from the first station 6 to the second station 7. The load-carrying tables 16b clockwise rotate around their own axes approximately by an angle of 90° in the course of traveling from the first station 6 to the second station 7. As a result, the diapers 50 held on the second load-carrying tables 16b, respectively, are clockwise turned round approximately by an angle of 90° in the course of traveling from the first station 6 to the second station 7.

The diapers 50 are transferred from the respective load-carrying tables 16a, 16b onto the second conveyor belt assembly 4 under the suction effect of the third suction mechanism as the load-carrying tables 16a, 16b reach the second station 7. The diapers 50 are held on the second conveyor belt assembly 4 under the suction effect with the respective front waist regions 51 thereof kept in contact with the second conveyor belt assembly 4. The first and second load-carrying tables 16a, 16b carrying the diapers 50 thereon, respectively, alternately reach the second station 7 and are successively transferred from the first and second load-carrying tables 16a, 16b onto the conveyor belt assembly 4.

In the case of this turning-round apparatus 1A, the inner cross-sectional area of the suction box 24 is reduced by the partition plate 45 and thereby a suction force of the suction box 24 is previously adjusted to be higher than a suction force of the suction box 43 so that the third suction mechanism can effectively function against the function of the first suction mechanism. At the second station 7, the ducts 20, 21 come just above the second opening 26c of the suction box 24 to establish air-communication between the ducts 20, 21 and the opening 26b. However, the suction force of the suction box 43 is higher than the suction force of the section box 24, so the third suction mechanism effectively functions against the function of the first suction mechanism and thereby allows the diapers 50 to be quickly transferred at the second station 7 from the respective load-carrying tables 16a, 16b onto the conveyor belt assembly 4.

After the diapers 50 have been transferred onto the second conveyor belt assembly 4, the load-carrying tables 16a, 16b move from the second station 7 toward the first station 6 as the rotary table 2 rotates. The first load-carrying tables 16a rotate around their own axes approximately by an angle of 90° in the peripheral zone 2a of the rotary table 2 while these first load-carrying tables 16a move along with the peripheral zone 2a of the rotary table 2 approximately by an angle of 90°. In other words, the first load-carrying tables 16a rotate around their own axes approximately by an angle of 270° in the peripheral zone 2a of the rotary table 2 in the course of traveling from the second station 7 to the first station 6. Thus the first load-carrying tables 16a rotate around their own axes counterclockwise (i.e., in the direction Z2) approximately by an angle of 360° in the peripheral zone-2a of the rotary table 2 as the rotary table 2 rotates clockwise (i.e., in the direction Z1) by an angle of 360° (i.e., as the first load-carrying tables 16a move from the first station 6 back to the first station 6). The second load-carrying tables 16b rotate around their own axes approximately by an angle of 90° in the peripheral zone 2a of the rotary table 2 as these second load-carrying tables 16b move along with the peripheral zone 2a of the rotary table 2 approximately by an angle of 90°. In other words, the second load-carrying tables 16b rotate around their own axes approximately by an angle of 360° clockwise (i.e., in the direction Z3) in the peripheral zone 2a of the rotary table 2 as the rotary table 2 clockwise (i.e., in the direction Z1) approximately by an angle of 360° (i.e., as the second load-carrying tables 16b move from the first station 6 back to the first station 6 again).

At the first station 6, the diapers 50 held on the first and second load-carrying tables 16a, 16b, respectively, have the waist-surrounding upper end zones 53 facing inward as viewed in the radial direction of the rotary table 2 (i.e., facing to the first shaft 5), as will be apparent from FIGS. 7 and 8. At the second station 7, the diapers 50 held on the first load-carrying tables 16a have the respective waist-surrounding upper end zones 53 facing in the direction in which the diapers 50 are conveyed by the conveyor belt assembly 4 (i.e., in the direction X2) and the diapers 50 held on the second load-carrying tables 16b have the respective crotch bottom zones 54 facing to the direction in which the diapers 50 are conveyed by the conveyor belt assembly 4 (i.e., in the direction X2). In the second station 7, therefore, the diapers 50 held on the second load-carrying tables 16b have been rotated substantially by an angle of 180° relative to the diapers 50 held on the first load-carrying tables 16a. The diapers 50 conveyed by the second and fourth conveyor belt assemblies 4, 40 are divided by a counter (not shown) into groups each comprising a predetermined number of the diapers 50 so that the diapers 50 may be conveniently packed in a package 65 as will be described later more in detail.

In the turning-round apparatus 1A, the load-carrying tables 16a, 16b move along with the peripheral zone 2a of the rotary table 2 and at the same time to rotate around their own axes in the peripheral zone 2a of the rotary table 2 so that the first load-carrying tables 16a are turned round approximately by an angle of 90° in the course of traveling from the first station 6 to the second station 7 while the second load-carrying tables 16b are turned round approximately by an angle of 90° in the direction opposite to the direction in which the first load-carrying tables 16a are turned round. In other words, the diapers 50 can be turned round approximately by an angle of 90° as these load-carrying tables 16a, 16b travel from the first station 6 to the second station 7. In addition, the diapers 50 held on the second load-carrying tables 16b can be turned round approximately by an angle of 90° in the direction opposite to the direction in which the diapers 50 held on the first load-carrying tables 16a are turned round and thereby the orientation of the diapers 50 held on the second load-carrying tables 16b can be shifted, in the second station 7, approximately by an angle of 180° from the orientation of the diapers 50 held on the first load-carrying tables 16a.

In the case of this turning-round apparatus 1A, the second station 7 is set at an angular distance of 90° from the first station 6 as viewed in the direction in which the rotary table 2 rotates. In other words, the direction in which the diapers 50 are conveyed by the second conveyor belt assembly 4 (i.e., the direction X2) can be turned round approximately by an angle of 90° relative to the direction in which the diapers 50 are conveyed by the first conveyor belt assembly 3 (i.e., the direction X1).

In this turning-round apparatus 1A, it is possible to pass the timing belt 30 on the belt-holding portion 27 and the pulleys 28 in open-fashion and to pass the timing belt 31 on the belt-holding portion 27 and the pulleys 29 in cross-fashion. In this case, clockwise rotation of the rotary table 2 causes the first load-carrying tables 16a to rotate around their own axes clockwise in the peripheral zone 2a of the rotary table 2 approximately by an angle of 90° in the course of traveling from the first station 6 to the second station 7 and simultaneously causes the second load-carrying tables 16b to rotate around their own axes counterclockwise in the peripheral zone 2a of the rotary table 2 approximately by an angle of 90° in the course of traveling from the first station 6 to the second station 7.

Figure 11:
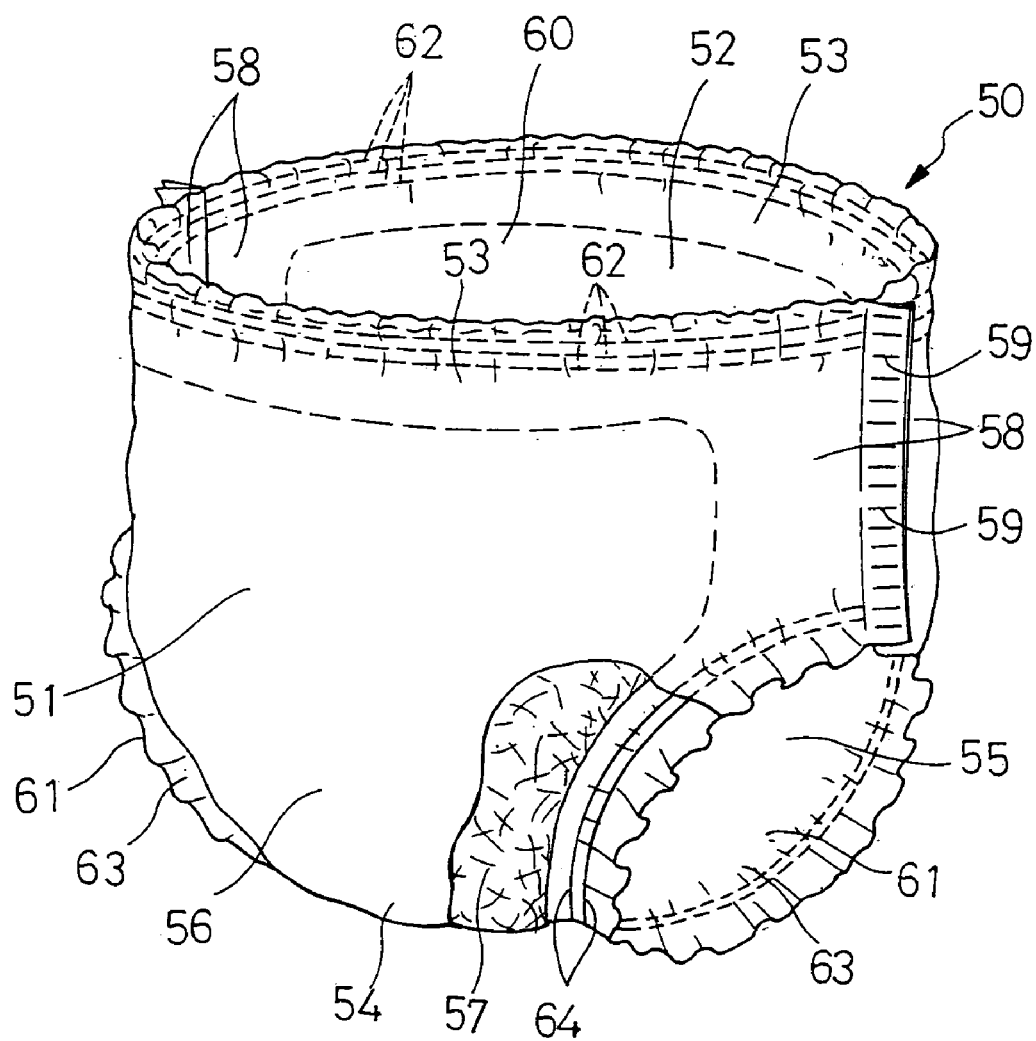
FIG. 11 is a partially cut away perspective view showing a diaper as a specific example of the article.
Figure 12:
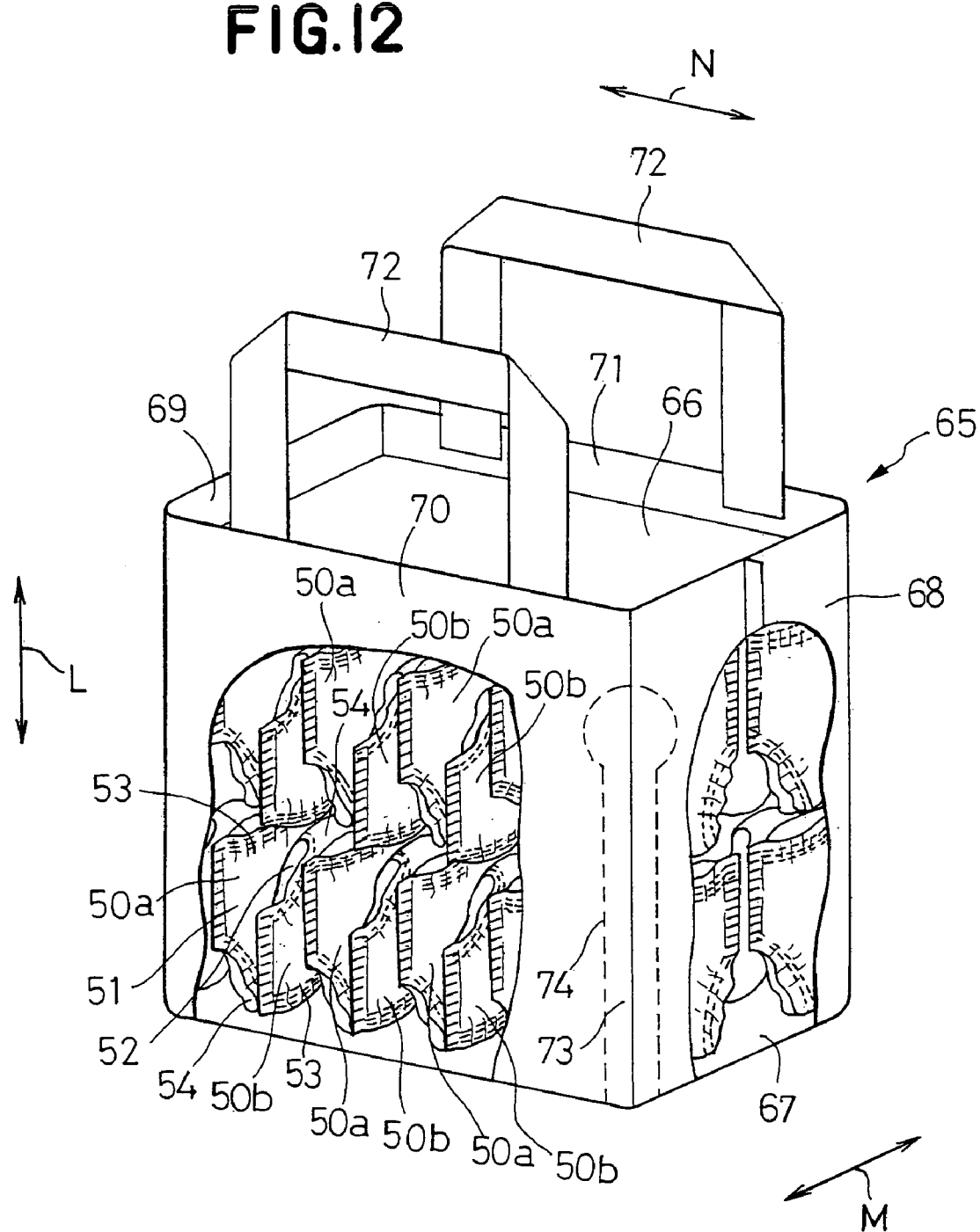
FIG. 12 is a partially cut away perspective view showing a packaged assembly comprising a package and a plurality of diapers as the specific example of the article packaged therein.

FIG. 11 is a partially cut away perspective view showing the diaper 50 as a specific example of the article and FIG. 12 is a partially cut away perspective view showing a packaged assembly comprising the package 65 and a plurality of the diapers 50 each as the specific example of the article. In FIG. 12, a vertical direction is indicated by an arrow L, a horizontal direction is indicated by an arrow M and a back-and-forth direction is indicated by an arrow N.

The diaper 50 comprises a liquid-pervious topsheet 55 facing a wearer's body, a liquid-impervious backsheet 56 facing away from the wearer's body and a liquid-absorbent core 57 interposed between these top- and backsheets 55, 56 and bonded to the inner surfaces of these sheets 55, 56. The front and rear waist regions 51, 52 of the diaper 50 are overlaid along transversely opposite waist lateral zones 58 and joined together by a plurality of heat-sealing lines 59 arranged intermittently along the transversely opposite waist lateral zones 58.

The diaper 50 is formed with a waist-hole 60 and a pair of leg-holes 61 lying below the waist-hole 60. The diaper 50 has the waist-surrounding upper end zone 53 and the crotch bottom zone 54 opposed to the waist-surrounding upper end zone 53. A plurality of waist elastic members 62 are attached to the waist-surrounding upper end zone 53 so that these elastic members 62 extend along the waist-hole 60 and can contract in this direction. A plurality of leg elastic members 64 are attached to leg-hole peripheral zones 63 so that these elastic members 64 extend along the respective leg-holes 61 and can contract in this direction. Portions of the top- and backsheets 55, 56 extending outward beyond a peripheral edge of the core 57 are and intermittently joined together.

The package 65 is formed by a flexible sheet and presents a substantially regular hexahedron which is relatively long in the back-and-forth direction and each pair of adjacent surfaces of which is orthogonal to each other. The package 65 is contoured by vertically opposed top and bottom surfaces 66, 67, first and second lateral surfaces 68, 69 opposed to each other in the back-and-forth direction, and transversely opposed third and fourth lateral surfaces 70, 71. The third and fourth lateral surfaces 70, 71 are provided with a pair of handling straps 72 describing circular arcs which are convex toward above the package 65. A corner 73 along which the first lateral surface 68 and the third lateral surface 70 intersect with each other is formed with perforations 74 extending in the vertical direction. In the case of the package 65, a region surrounded by the perforations 74 may be torn off from the package 65 to form this corner 73 with a dispensing port for the individual diapers 50.

First diapers 50a transferred from the first conveyor belt assembly 3 onto the first load-carrying tables 16a and second diapers 50b transferred from the first conveyor belt assembly 3 onto the second load-carrying tables 16b are closely packed into a space defined between the first lateral surface 68 and the second lateral surface 69 in a manner that these diapers 50a, 50b may be placed against one another in the back-and-forth direction. In the package 65, these diapers 50a, 50b are alternately arranged so that the each of the second diapers 50b may be interposed between each pair of the diapers 50a.

Within the package 65, the front waist region 51 of the adjacent diapers 50a and the rear waist regions 52 of the diapers 40b are placed against each other under in a compression state. Within the package 65, two groups each comprising a predetermined number of the diapers 50 are placed upon each other in the vertical direction and such two groups are placed side by side. In this manner, four groups of the diapers 50a, 50b are packed in the package 65. The first diapers 50a have their waist-surrounding upper end zones 53 put aside relative to their crotch bottom zones 54 toward the top surface 66 of the package 65. The second diapers 50b have their waist-surrounding upper end zones 53 put aside relative to their crotch bottom zones 54 toward the bottom surface 67 of the package 65.

Figure 13:
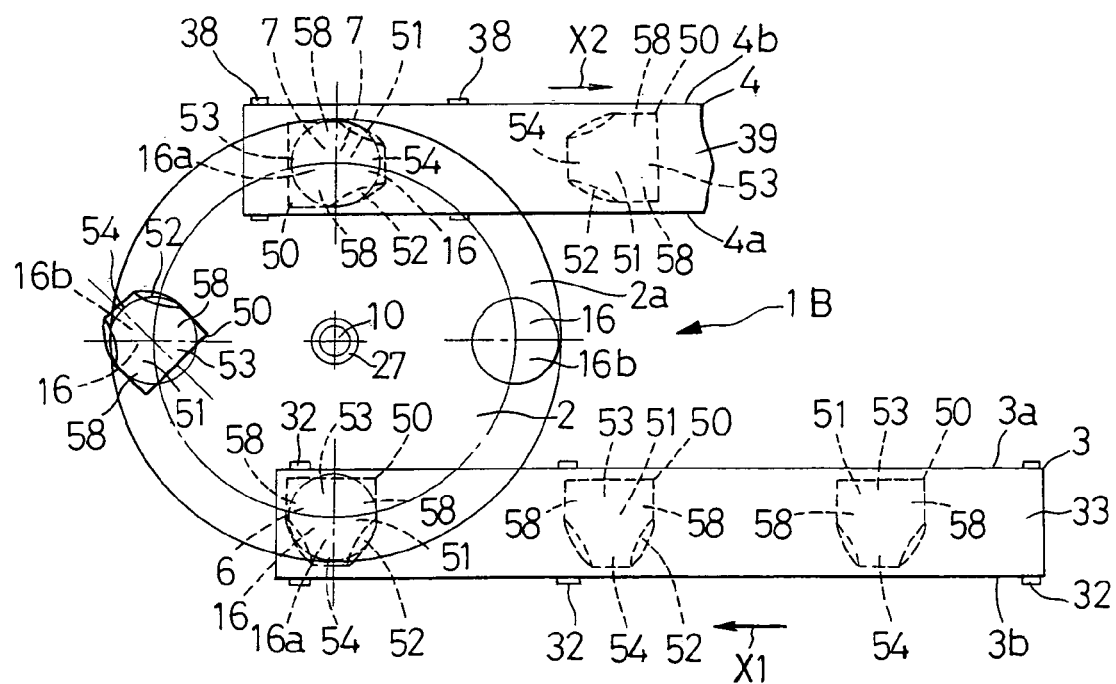
FIG. 13 is a top view showing the article turning-round apparatus according to a preferred embodiment of the invention.
Figure 14:
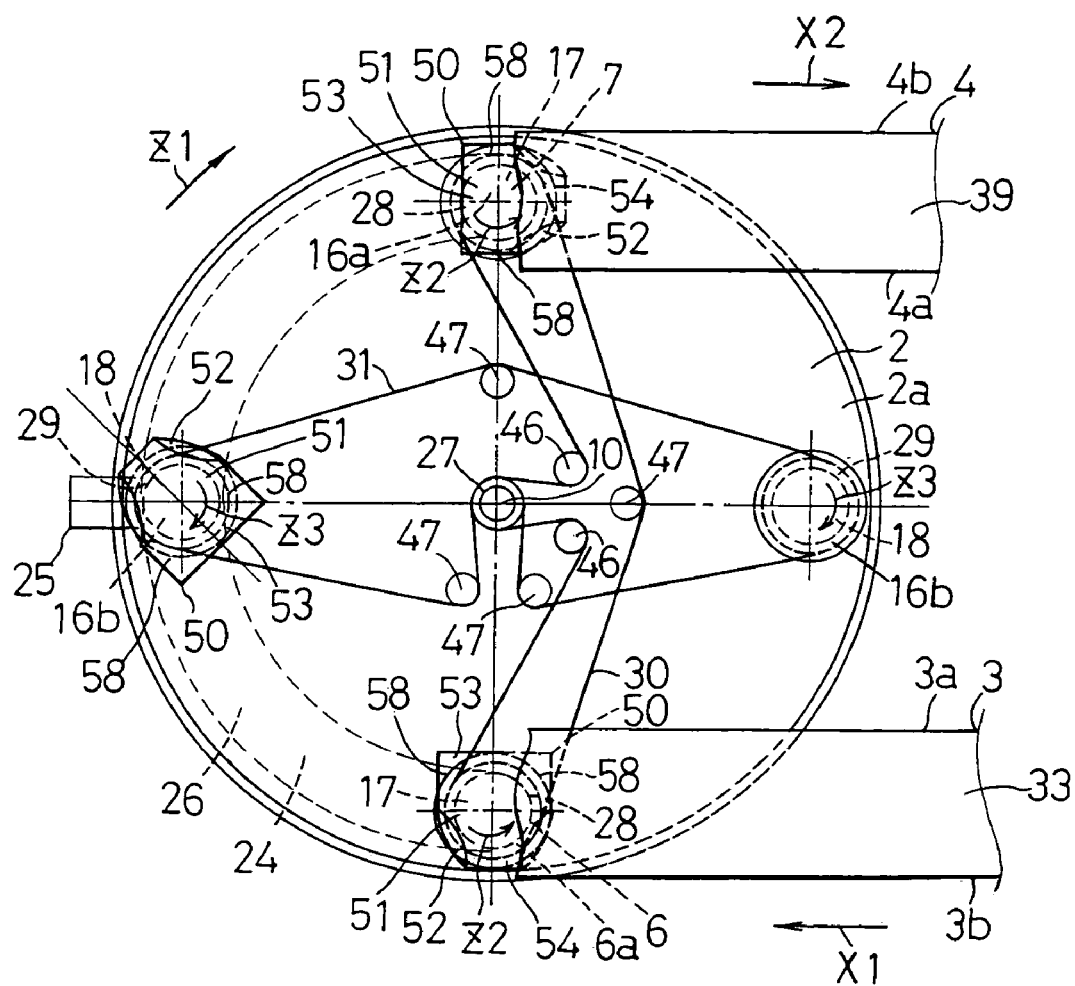
FIG. 14 is a partially cutaway scale-enlarged top view showing the article turning-round apparatus of FIG. 13 with the first and second conveyor belt assemblies.
Figure 15:
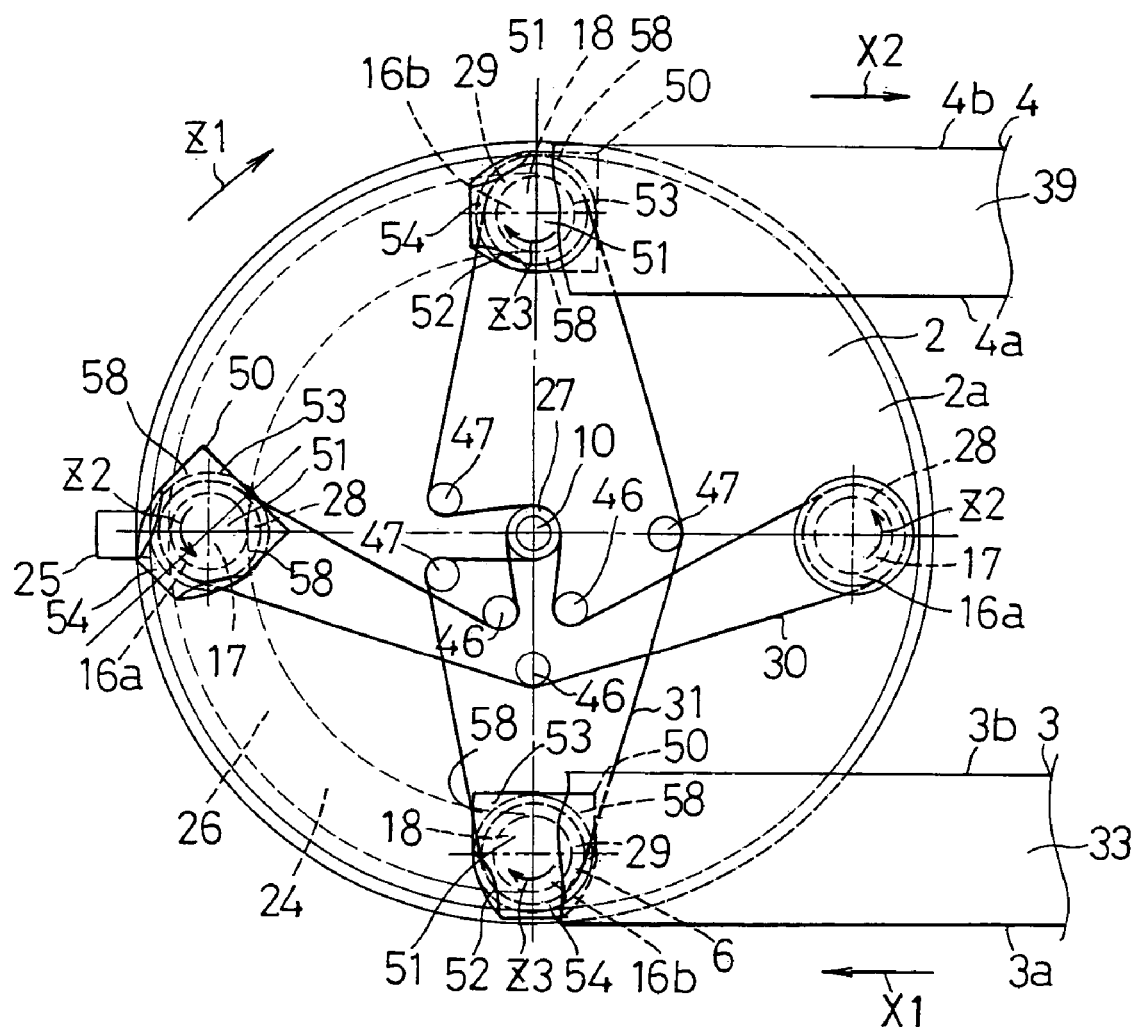
FIG. 15 is a partially cutaway scale-enlarged top view showing the article turning-round apparatus of FIG. 13 with the first and second conveyor belt assemblies.

FIG. 13 is a top view showing the article turning-round apparatus 1B according to a preferred embodiment of the invention and FIGS. 14 and 15 are scale-enlarged top views showing the article turning-round apparatus 1B of FIG. 13 with the first and second conveyor belt assemblies 3, 4 partially cut away. In FIG. 13, the timing belts 30, 31 are not shown and, in FIGS. 14 and 15, the suction boxes 37, 43 are not shown. FIG. 14 illustrates the first load-carrying tables 16a having reached the first and second stations 6, 7 of the rotary table 2, respectively, and FIG. 15 illustrates the second load-carrying tables 16b having reached the first and second stations 6, 7 of the rotary table 2, respectively.

The turning-round apparatus 1B comprises the rotary table 2 (rotary base) provided with a plurality of the load-carrying tables 16, the first conveyor belt assembly 3 serving to convey the diapers 50 onto the rotary table 2 and the second conveyor belt assembly 4 serving to convey the diapers 50 away from the rotary table 2.

The rotary table 2 rotates around the first shaft 5. The peripheral zone 2a of the rotary table 2 is provided with the first station 6 at which the diapers 50 are loaded from the first conveyor belt assembly 3 onto the rotary table 2 and the second station 7 at which the diapers 50 are unloaded from the rotary table onto the second conveyor belt assembly 4. The second station 7 corresponds to the position along the peripheral zone 2a of the rotary table 2 at which the rotary table 2 has been rotated by an angle of 180° from the first station 6 (i.e., the second station 7 is located at an angular distance of 180° from the first station 6). The first shaft 5 has its peripheral surface covered with the stationary frame 8 and contains the stationary shaft 10 inserted through the first shaft 5. A rotational force is transmitted from the electric motor by means of the drive belt 15 to the first shaft 5 so as to be rotated between the stationary frame 8 and the stationary shaft 10 (See FIGS. 2 and 3). The stationary shaft 10 can not rotate since its lower end 10a is connected with a locking member 13. Rotation of the first shaft 5 causes the rotary table 2 to rotate in the same direction as the direction in which the first shaft 5 rotates.

The load-carrying tables 16 are mounted on the upper surface of the rotary table 2 along the peripheral zone 2a at regular intervals in the circumferential direction of the rotary table 2. The load-carrying tables 16 comprise the first load-carrying tables 16a mounted on the rotary table 2 so as to be rotatable around the respective second shafts 17 (i.e., around the ducts 20) and the second load-carrying tables 16b mounted on the rotary table 2 so as to be rotatable around the respective third shafts 18 (i.e., around the ducts 21). These first and second load-carrying tables 16a, 16b are alternately arranged along the peripheral zone 2a of the rotary table 2.

The first load-carrying tables 16a move along with the peripheral zone 2a of the rotary table 2 and simultaneously rotate around their own axes in the peripheral zone 2a of the rotary table 2 by means of the respective second shafts 17 as the rotary table 2 rotates. The second load-carrying tables 16b also move along with the peripheral zone 2a of the rotary table 2 and simultaneously rotate around their own axes in the peripheral zone 2a of the rotary table 2 by means of the respective third shafts 18. The first and second load-carrying tables 16a, 16b have the first suction mechanism. The first suction mechanism is same as that illustrated in FIG. 4, wherein the air is sucked through the duct 25 into the suction box 24 and thereby a pressure within inner spaces of the respective ducts 20, 21 is maintained at a negative level.

An upper end 10b of the stationary shaft 10 is provided thereon with the belt-holding portion 27 and the second shafts 17 (i.e., the ducts 20) of the first load-carrying tables 16a are provided thereon with the pulleys 28, 28. Timing belts 30 are passed on the belt-holding portion 27 and the pulleys 28, 28 in open-fashion (See FIG. 9). The belt-holding portion 27 and the pulleys 28 have an effective radius ratio (a rotational velocity ratio) of 1:2. Clockwise rotation of the rotary table 2 (i.e., in the direction Z1) causes the first load-carrying tables 16a to travel from the first station 6 to the second station 7 along with the peripheral zone 2a of the rotary table 2 approximately by an angle of 180°. Thus a turning force is transmitted by the belt 30 to the pulleys 28 and thereby the first load-carrying tables 16a rotate around their own axes counterclockwise (in the direction Z2) approximately by an angle of 90° together with the respective ducts 20 in the peripheral zone 2a of the rotary table 2.

The third shafts 18 (i.e., ducts 21) of the respective second load-carrying tables 16b are provided thereon with the pulleys 29. Timing belt 31 is passed on the belt-holding portion 27 and the pulleys 29 in cross-fashion (See FIG. 10). The belt-holding portion 27 and the pulleys 29 have an effective radius ratio (a rotational velocity ratio) of 1:2. Clockwise rotation of the rotary table 2 (i.e., in the direction Z1) causes the second load-carrying tables 16b to travel from the first station 6 to the second station 7 along with the peripheral zone 2a of the rotary table 2 approximately by an angle of 180°. Thus a turning force is transmitted by the belt 31 to the pulleys 29 and thereby the second load-carrying tables 16b rotate around their own axes clockwise (in the direction Z3) approximately by an angle of 90° together with the respective ducts 21 in the peripheral zone 2a of the rotary table 2.

The first conveyor belt assembly 3 comprises a plurality of belt pulleys 32 and a belt 33 passed on these belt pulleys 32. Below the first conveyor belt assembly 3, there is provided a third conveyor belt assembly 34 comprising belt pulleys 35 and a belt 36 passed on these belt pulleys 35. The belt 36 circularly runs in synchronization with the belt 33. The first conveyor belt assembly 3 extends toward the peripheral zone 2a of the rotary table 2 so as to reach the first station 6 on the upper surface of the rotary table 2. The third conveyor belt assembly 34 extends toward the peripheral zone 2a of the rotary table 2 so as to terminate short of the outer side edge of the rotary table 2 (See FIG. 4).

The first conveyor belt assembly 3 is provided with a second suction mechanism serving to hold the diapers 50 under a suction effect. The second suction mechanism is similar to that illustrated in FIG. 4 in that the air is sucked into the suction box 37 so that the air may flow from the outer side to the inner side of the belt 33 and thereby a suction force is generated through the belt 33. The diapers 50 are held between the first conveyor belt assembly 3 and the third conveyor belt assembly 34 and conveyed at the regular intervals in this sandwiched state to the first station 6 of the rotary table 2. On the conveyor belt assembly 3, these diapers 50 have their waist-surrounding upper end zones 53 being lined up in the direction in which the diapers 50 are conveyed (i.e., in the direction X1) and their crotch bottom zones 54 also being lined up in the direction in which the diapers 50 are conveyed (i.e., in the direction X1).

The second conveyor belt assembly 4 comprises a plurality of the belt pulleys 38 and the belt 39 passed on these belt pulleys 38. Below the second conveyor belt assembly 4, there is provided a fourth conveyor belt assembly 40 comprising a plurality of the belt pulleys 41 and a belt 42 passed on these belt pulleys 41. The belt 42 circularly runs in synchronization with the belt 39. The second conveyor belt assembly 4 extends toward the peripheral zone 2a of the rotary table 2 so as to reach the second station 7 on the upper surface of the rotary table 2. The fourth conveyor belt assembly 40 extends toward the peripheral zone 2a of the rotary table 2 so as to terminate short of the outer side edge of the rotary table 2 (See FIG. 5).

The second conveyor belt assembly 4 is provided with the third suction mechanism serving to suck the diapers 50 and thereby to hold them. The third suction mechanism is similar to that illustrated in FIG. 5 in that the air is sucked into the suction box 43 so that the air may flow from the outer side toward the inner side of the belt 39 and a suction force may be generated through the belt 39. The diapers 50 are held between the second conveyor belt assembly 4 and the fourth conveyor belt assembly 40 and conveyed away at the regular intervals in this state from the second station 7 outward of the rotary table 2. On the conveyor belt assembly 4, each pair of the adjacent diapers 50 have the respective waist-surrounding upper end zones 53 opposed to each other and a pair of the diapers 50 overlapping the aforementioned pair of the diapers 50 have the respective transversely opposite waist lateral zones 58 lined up parallel to the inner and outer side edges 4a, 4b of the conveyor belt assembly 4, respectively.

In this turning-round apparatus 1B, in parallel with conveyance of the diapers 50 by means of those conveyor belt assemblies 3, 34 to the first station 6, any one of the first load-carrying tables 16a or the second load-carrying tables 16b reaches the first station 6. Thereupon the ducts 20, 21 come just above the first opening 26a of the suction box 24 and the first suction mechanism associated with the load-carrying tables 16a, 16b is actuated. In the turning-round apparatus 1B also, the first suction mechanism effectively functions against the effect of the second suction mechanism so that, at the first station 6, the diapers 50 are transferred from the conveyor belt assembly 3 onto the load-carrying tables 16a, 16b and held on the load-carrying tables 16a, 16b under the suction effect.

The first load-carrying tables 16a and the second load-carrying tables 16b carrying the diapers 50 thereon, respectively, move along with the peripheral zone 2a of the rotary table 2 from the first station 6 toward the second station 7 of the rotary table 2 as the rotary table 2 rotates clockwise (i.e., in the direction Z1). The first load-carrying tables 16a rotate counterclockwise (i.e., in the direction Z2) on their own axes approximately by an angle of 90° as these load-carrying tables 16a move from the first station 6 to the second station 7. The second load-carrying tables 16b rotate clockwise (i.e., in the direction Z3) on their own axes approximately by an angle of 90° as these load-carrying tables 16b move from the first station 6 to the second station 7.

At the first station 6, the respective waist-surrounding upper end zones 53 of the diapers 50 held on the first and second load-carrying tables 16a, 16b face inward to the radial direction of the rotary table 2 (i.e., facing to the first shaft 5), as will be apparent from FIGS. 14 and 15. At the second station 7, the respective waist-surrounding upper end zones 53 of the diapers 50 held on the first load-carrying tables 16a face to the direction in which the diapers 50 are conveyed by the conveyor belt assembly 4 (i.e., in the direction X2) while the respective waist-surrounding upper end zones 53 of the diapers 50 held on the second load-carrying tables 16b face to the direction corresponding to the direction in which the diapers 50 are conveyed by the conveyor belt assembly 4 (i.e., in the direction X2).

The diapers 50 are successively transferred from the load-carrying tables 16a, 16b onto the second conveyor belt assembly 4 under the effect of the third suction mechanism as these load-carrying tables 16a, 16b reach the second station 7. The diapers 50 have the respective front waist regions 51 held on the conveyor belt assembly 4 under the suction effect. In this turning-round apparatus 1B, the third suction mechanism can effectively function against the function of the first suction mechanism and thereby allows the diapers 50, at the second station 7, to be quickly transferred from the respective load-carrying tables 16a, 16b onto the conveyor belt assembly 4.

After the diapers 50 have been transferred onto the second conveyor belt assembly 4, the load-carrying tables 16a, 16b move from the second station 7 toward the first station 6 as the rotary table 2 rotates. The first load-carrying tables 16a rotate around their own axes in the peripheral zone 2a of the rotary table 2 approximately by an angle of 90° while the first load-carrying tables 16a move along with the peripheral zone 2a of the rotary table 2 approximately by an angle of 180°. In other words, the first lead-carrying tables 16a rotate around their own axes in the peripheral zone 2a of the rotary table approximately by angle of 90° in the course of movement from the second station 7 to the first station 6. More specifically, the first load-carrying tables 16a rotate around their own axes counterclockwise (i.e., in the direction Z2) approximately by an angle of 180° as the rotary table 2 rotates clockwise (i.e., in the direction Z1) approximately by an angle of 360°. The second load-carrying tables 16b rotate around their own axes in the peripheral zone 2a of the rotary table 2 approximately by an angle of 90° as these second load-carrying tables 16b move along with the peripheral zone 2a of the rotary table 2 approximately by an angle of 180°. In other words, the second load-carrying tables 16b rotate around their own axes in the peripheral zone 2a of the rotary table 2 approximately by an angle of 90° in the course of movement from the second station 7 to the first station 6. More specifically, these second load-carrying tables 16b rotate around their own axes clockwise (i.e., in the direction Z3) in the peripheral zone 2a of the rotary table 2 approximately by an angle of 180° as the rotary table 2 rotates clockwise (i.e., in the direction Z1) by an angle of 360°. The diapers 50 having been conveyed away by the second and fourth conveyor belt assemblies 4, 40 are divided into groups each comprising a predetermined number of the diapers 50 by the counter in the same manner as has been described in reference with FIG. 1 so that the diapers 50 may be conveniently packed in the package 65 (See FIG. 11).

This turning-round apparatus 1B allows the diapers 50 to be turned round approximately by an angle of 90° as the first and second load-carrying tables 16a, 16b move from the first station 6 to the second station 7. In addition, the diapers 50 held on the second load-carrying tables 16b can be turned round approximately by an angle of 90° in the direction opposite to the direction in which the diapers 50 held on the first load-carrying tables 16a are turned round and thereby the orientation of the diapers 50 held on the second load-carrying tables 16b can be shifted, in the second station 7, approximately by an angle of 180° from the orientation of the diapers 50 held on the first load-carrying tables 16a.

Figure 16:
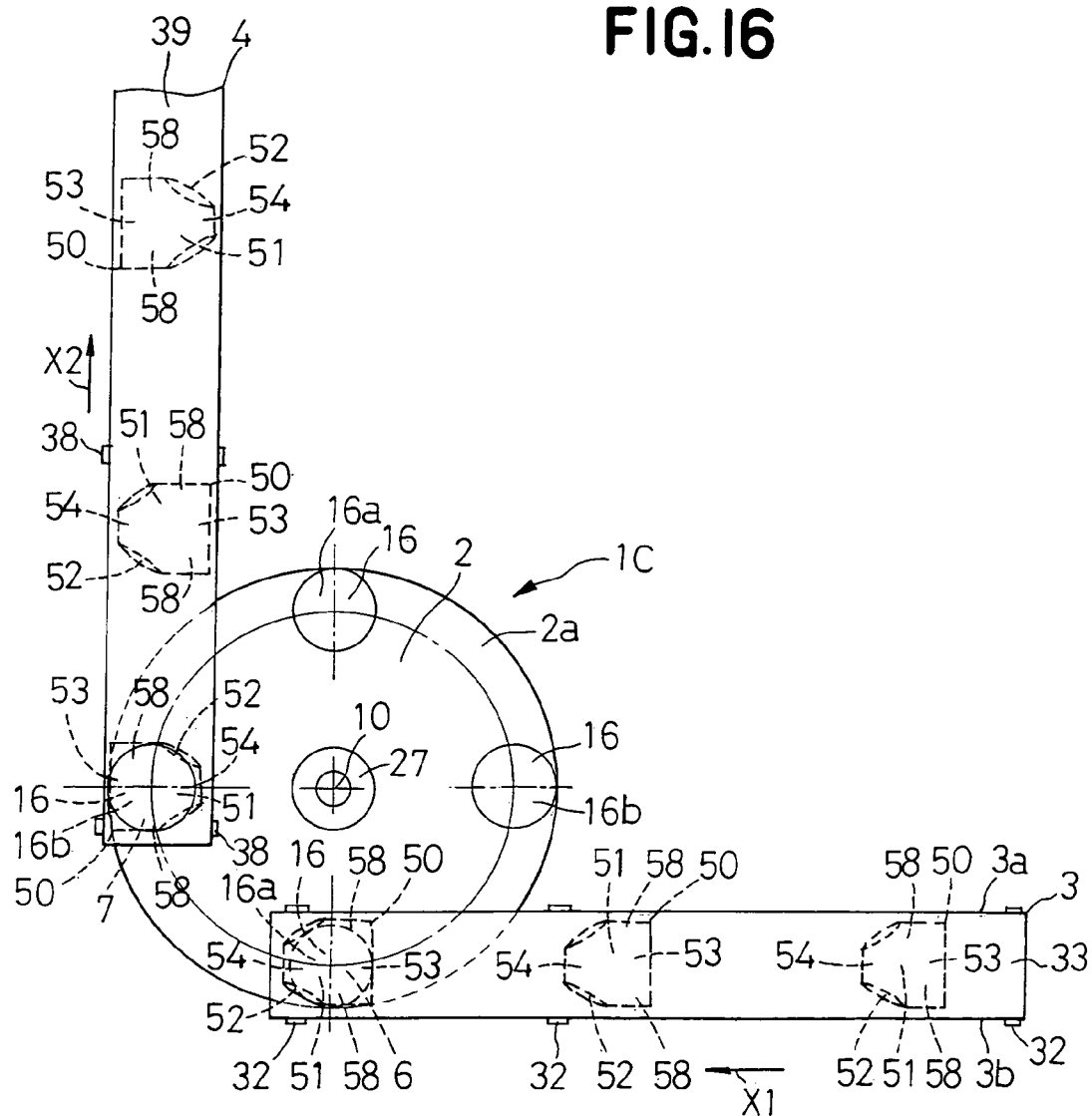
FIG. 16 is a top view showing the article turning-round apparatus according to still another embodiment of the invention.
Figure 17:
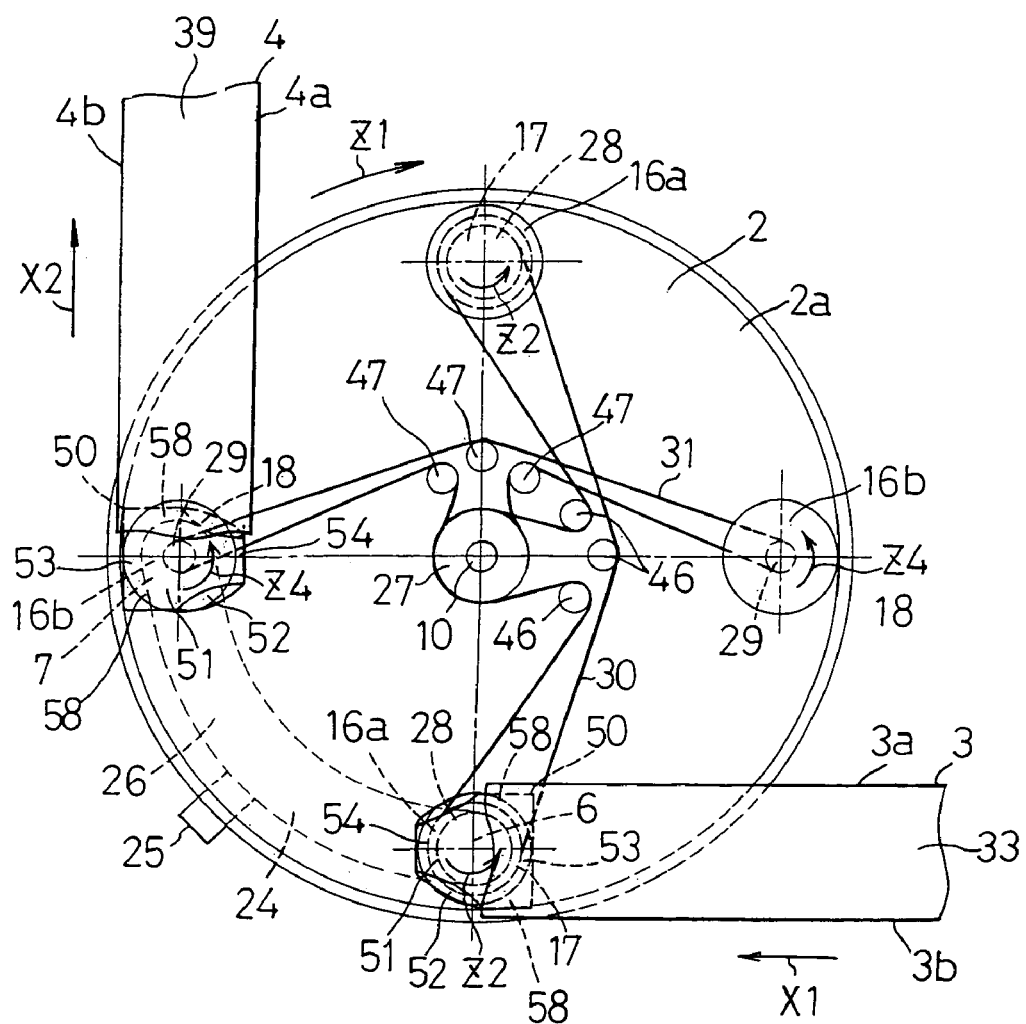
FIG. 17 is a partially cutaway scale-enlarged top view showing the article turning-round apparatus of FIG. 16 with the first and second conveyor belt assemblies.
Figure 18:
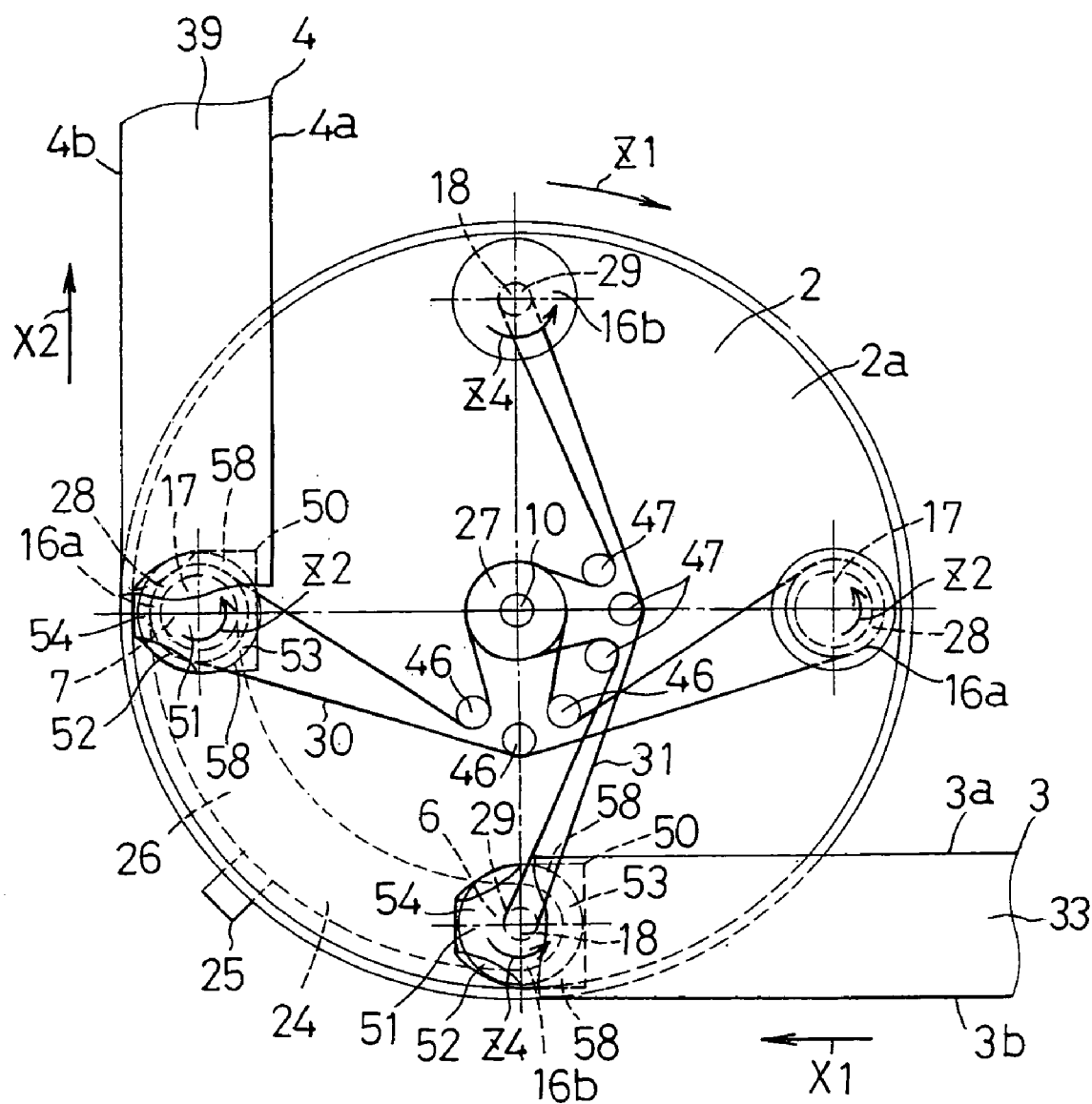
FIG. 18 is a partially cutaway scale-enlarged top view showing the article turning-round apparatus of FIG. 16 with the first and second conveyor belt assemblies.

FIG. 16 is a top view showing the article turning-round apparatus 1C according to still another embodiment of the invention, FIG. 17 is a partially cutaway scale-enlarged top view showing the article turning-round apparatus 1C of FIG. 16 with the first and second conveyor belt assemblies 3, 4 and FIG. 18 also is a partially cutaway scale-enlarged top view showing the article turning-round apparatus 1C of FIG. 16 with the first and second conveyor belt assemblies 3, 4. In FIG. 16, the timing belts 30, 31 are not shown and, in FIGS. 17 and 18, the suction boxes 37, 43 are not shown. FIG. 17 illustrates a state of the apparatus 1C in which one of the first load-carrying tables 16a has reached the first station 6 of the rotary table 2 and one of the second load-carrying tables 16b has reached the second station 7 of the rotary table 2. FIG. 18 illustrates a state of the apparatus 1C in which one of the second load-carrying tables 16b has reached the first station 6 of the rotary table 2 and one of the first load-carrying tables 16a has reached the second station 7 of the rotary table 2.

The turning-round apparatus 1C comprises the rotary table 2 (rotary base) provided with a plurality of the load-carrying tables 16, the first conveyor belt assembly 3 serving to convey the diapers 50 onto the rotary table 2 and the second conveyor belt assembly 4 serving to convey the diapers 50 away from the rotary table 2.

The rotary table 2 rotates around the first shaft 5. The peripheral zone 2a of the rotary table 2 is provided with the first station 6 at which the diapers 50 are loaded from the first conveyor belt assembly 3 onto the rotary table 2 and the second station 7 at which the diapers 50 are unloaded from the rotary table 2 onto the second conveyor belt assembly 4. The second station 7 corresponds to a position along the peripheral zone 2a of the rotary table 2 at which the rotary table 2 has been rotated by an angle of 90° from the first station 6 (i.e., the second station 7 is located at an angular distance of 90° from the first station 6). The first shaft 5 has its peripheral surface covered with a stationary frame 8 and contains a stationary shaft 10 inserted through the first shaft 5. A rotational force is transmitted from the electric motor by means of a drive belt 15 to the first shaft 5 so as to be rotated between the stationary frame 8 and the stationary shaft 10 (See FIGS. 2 and 3). The stationary shaft 10 can not rotate since its lower end 10a is connected with a locking member 13. Rotation of the first shaft 5 causes the rotary table 2 to rotate in the same direction as the direction in which the first shaft 5 rotates.

The load-carrying tables 16 are mounted on the upper surface of the rotary table 2 along the peripheral zone 2a at regular intervals in the circumferential direction of the rotary table 2. The load-carrying tables 16 comprise first load-carrying tables 16a mounted on the rotary table 2 so as to be rotatable around the respective second shafts 17 (i.e., the ducts 20) and second load-carrying tables 16b mounted on the rotary table 2 so as to be rotatable around the respective third shafts 18 (i.e., around the ducts 21). These first and second load-carrying tables 16a, 16b are alternately arranged along the peripheral zone 2a of the rotary table 2.

The first load-carrying tables 16a move along with the peripheral zone 2a of the rotary table 2 and simultaneously rotate around their own axes as the rotary table 2 rotates. The second load-carrying tables 16b also move along with the peripheral zone 2a of the rotary table 2 and simultaneously rotate around their own axes by means of the respective third shafts 18 as the rotary table 2 rotates. The first and second load-carrying tables 16a, 16b have the first suction mechanism. The first suction mechanism is same as that illustrated by FIG. 4, wherein the air within the ducts 20, 21 is sucked through the duct 25 into a suction box 24 and a pressure within inner spaces of the respective ducts 20, 21 is maintained at a negative level.

An upper end 10b of the stationary shaft 10 is provided thereon with the belt-holding portion 27. The second shafts 17 (i.e., the ducts 20) of the first load-carrying tables 16a are provided thereon with pulleys 28. The timing belt 30 is passed on elements 27, 28 in open-fashion (See FIG. 9). An effective radius ratio (a rotational velocity ratio) between the belt-holding portion 27 and the pulleys 28 is 1:1. Clockwise rotation of the rotary table 2 (in the direction Z1) causes the first load-carrying tables 16a to move along with the peripheral zone 2a of the rotary table 2 approximately by an angle of 90° from the first station 6 toward the second station 7. Thus a turning force is transmitted by the belt 30 to the pulleys 28 and thereby the first load-carrying tables 16a rotate around their own axes in the peripheral zone 2a of the rotary table 2 counterclockwise (in the direction Z2) together with the respective ducts 20 approximately by an angle of 90°.

The third shafts 18 (i.e., the ducts 21) of the second load-carrying tables 16b are provided thereon with the pulleys 29. The timing belt 31 is passed on elements 27, 29 in open-fashion (See FIG. 10). An effective radius ratio (a rotational velocity ratio) between the belt-holding portion 27 and the pulleys 29 is 3:1. Clockwise rotation of the rotary table 2 (in the direction Z1) causes the second load-carrying tables 16b to move along with the peripheral zone 2a of the rotary table 2 approximately by an angle of 90° from the first station 6 toward the second station 7. Thus a turning force is transmitted by the belt 31 to the pulleys 29 and thereby the second load-carrying tables 16b rotate around their own axes in the peripheral zone 2a of the rotary table 2 counterclockwise (in a direction indicated by an arrow Z4) together with the respective ducts 21 approximately by an angle of 270°.

The first conveyor belt assembly 3 comprises a plurality of the belt pulleys 32 and the belt 33 passed on these belt pulleys 32. Below the first conveyor belt assembly 3, there is provided the third conveyor belt assembly 34 comprising a plurality of the belt pulleys 35 and the belt 36 passed on these belt pulleys 35. The belt 36 circularly runs in synchronization with the belt 33. The first conveyor belt assembly 3 extends toward the peripheral zone 2a of the rotary table 2 so as to reach the first station 6 on the upper surface of the rotary table 2. The third conveyor belt assembly 34 extends toward the peripheral zone 2a of the rotary table 2 so as to terminate short of the peripheral zone 2a of the rotary table 2 (See FIG. 4).

The first conveyor belt assembly 3 is provided with the second suction mechanism serving to suck the diapers 50 and thereby to hold them. The second suction mechanism is similar to that illustrated by FIG. 4 in that the air is sucked into the suction box 37 so that the air may flow from the outer side to the inner side of the belt 33 and thereby a suction force is generated through the belt 33. The diapers 50 are held between the first conveyor belt assembly 3 and the third conveyor belt assembly 34 and conveyed at the regular intervals in this state to the first station 6 of the rotary table 2. On the conveyor belt assembly 3, each pair of the adjacent diapers 50 respectively have the waist-surrounding upper end zones 53 and the crotch bottom zones 54 opposed to each other and the transversely opposite waist lateral zones 58 extending parallel to the inner and outer side edges 3a, 3b of the conveyor belt assembly 3.

The second conveyor belt assembly 4 comprises a plurality of the belt pulleys 38 and the belt 39 passed on these belt pulleys 38. Below the second conveyor belt assembly 4, there is provided the fourth conveyor belt assembly 40 comprising a plurality of the belt pulleys 41 and the belt 42 passed on these belt pulleys 41. The belt 42 circularly runs in synchronization with the belt 39. The second conveyor belt assembly 4 extends toward the peripheral zone 2a of the rotary table 2 so as to reach the second station 7 on the upper surface of the rotary table 2. The fourth conveyor belt assembly 40 extends toward the peripheral zone 2a of the rotary table 2 so as to terminate short of the peripheral zone 2a of the rotary table 2 (See FIG. 5).

The second conveyor belt assembly 4 is provided with the third suction mechanism serving to suck the diapers 50 and thereby to hold them. The third suction mechanism is similar to that illustrated in FIG. 5 in that the air is sucked into the suction box 43 so that the air may flow from the outer side toward the inner side of the belt 39 and a suction force may be generated through the belt 39. The diapers 50 are held between the second conveyor belt assembly 4 and the fourth conveyor belt assembly 40 and conveyed away at the regular intervals in this state from the second station 7 outward of the rotary table 2. On the conveyor belt assembly 4, each pair of the adjacent diapers 50 have the waist-surrounding upper end zones 53 and the crotch bottom zones 54 lined up one with another in the direction in which the diapers 50 are conveyed (i.e., in the direction X2) and the transversely opposite waist lateral zones 58 opposed one to another as viewed in the direction in which the diapers 50 are conveyed (i.e., the direction X2).

In this turning-round apparatus 1C, in parallel with conveyance of the diapers 50 by means of those conveyor belt assemblies 3, 34 to the first station 6, any one of the first load-carrying tables 16a or the second load-carrying tables 16b reaches the first station 6 and comes just above the first opening 26a of the suction box 24. Thereupon the first suction mechanism associated with the load-carrying tables 16a, 16b is actuated. In the turning-round apparatus 1C also, the first suction mechanism effectively functions against the effect of the second suction mechanism so that, at the first station 6, the diaper 50 is quickly transferred from the conveyor belt assembly 3 onto the load-carrying tables 16a, 16b and held on the load-carrying tables 16a, 16b under the suction effect.

The first load-carrying tables 16a and the second load-carrying tables 16b carrying the diapers 50 thereon, respectively, move along with the peripheral zone 2a of the rotary table 2 from the first station 6 toward the second station 7 of the rotary table 2 as the rotary table 2 rotates clockwise (i.e., in the direction Z1). In the course of traveling from the first station 6 to the second station 7, the first load-carrying tables 16a rotate counterclockwise (i.e., in the direction Z2) on their own axes approximately by an angle of 90° and the second load-carrying tables 16b rotate counterclockwise (i.e., in the direction Z4) on their own axes approximately by an angle of 270°.

At the first station 6, the respective crotch bottom zones 53 of the diapers 50 held on the first and second load-carrying tables 16a, 16b face to the direction in which the diapers 50 are conveyed by the conveyor belt assembly 3 (i.e., in the direction X1) as will be apparent from FIGS. 17 and 18. At the second station 7, the respective waist-surrounding upper end zones 53 of the diapers 50 held on the first load-carrying tables 16a face inward to the radial direction of the rotary table 2 (i.e., face to the first shaft 5) while the respective waist-surrounding upper end zones 53 of the diapers 50 held on the second load-carrying tables 16b face outward to the radial direction of the rotary table 2 (facing the peripheral zone 2a of the rotary table 2).

The diapers 50 are successively transferred from the load-carrying tables 16a, 16b onto the second conveyor belt assembly 4 under the effect of the third suction mechanism as these load-carrying tables 16a, 16b reach the second station 7. The diapers 50 have their front waist regions 51 held on the conveyor belt assembly 4 under the suction effect. In this turning-on apparatus 1C, the third suction mechanism can effectively function against the function of the first suction mechanism and thereby allows the diapers 50, at the second station, to be quickly transferred from the respective load-carrying tables 16a, 16b onto the conveyor belt assembly 4.

After the diapers 50 have been transferred onto the second conveyor belt assembly 4, the load-carrying tables 16a, 16b move from the second station 7 toward the first station 6 as the rotary table 2 rotates. The first load-carrying tables 16a rotate in the peripheral zone 2a of the rotary table 2 around their own axes approximately by an angle of 90° as these first load-carrying tables 16a move along with the peripheral zone 2a of the rotary table 2 approximately by an angle of 90°. In other words, the first load-carrying tables 16a rotate in the peripheral zone 2a of the rotary table 2 around their own axes approximately by an angle of 270° as these first load-carrying tables 16a move from the second station 7 to the first station 6. Thus the first load-carrying tables 16a rotate counterclockwise (i.e., in the direction Z2) in the peripheral zone 2a of the rotary table 2 around their own axes approximately by an angle of 360° as these first load-carrying tables 16a move clockwise (i.e., in the direction Z1) along with the peripheral zone 2a of the rotary table 2. The second load-carrying tables 16b rotate around their own axes approximately by an angle of 270° in the peripheral zone 2a of the rotary table 2 as these second load-carrying tables 16b move along with the peripheral zone 2a of the rotary table 2 approximately by an angle of 90°. In other words, the second load-carrying tables 16b rotate in the peripheral zone 2a of the rotary table 2 around their own axes approximately by an angle of 810° as these second load-carrying tables 16b move from the second station 7 to the first station 6. More specifically, these second load-carrying tables 16b rotate counterclockwise (i.e., in the direction Z4) around their own axes approximately by an angle of 1080° in the peripheral zone 2a of the rotary table 2 as the rotary table 2 rotates clockwise (i.e., in the direction Z1) by an angle of 360°. The diapers 50 having been conveyed by the second conveyor belt assembly 4 are divided into groups each comprising a predetermined number of the diapers 50 by the counter in the same manner as has been described in reference with FIG. 1 so that the diapers 50 may be conveniently packed in the package 65 (See FIG. 11).

This turning-round apparatus 1C allows the diapers 50 to be turned round approximately by an angle of 90° as the first and second load-carrying tables 16a, 16b move from the first station 6 to the second station 7. In addition, the diapers 50 held on the second load-carrying tables 16b can be turned round approximately by an angle of 90° in the direction opposite to the direction in which the diapers 50 held on the first load-carrying tables 16a are turned round and thereby the orientation of the diapers 50 held on the second load-carrying tables 16b can be shifted, in the second station 7, approximately by an angle of 180° from the orientation of the diapers 50 held on the first load-carrying tables 16a.

In the case of this turning-round apparatus 1C, the second station 7 is set at an angular distance of 90° from the first station 6 as viewed in the direction in which the rotary table 2 rotates. In other words, the direction in which the diapers 50 are conveyed by the second conveyor belt assembly 4 (i.e., the direction X2) can be turned round approximately by an angle of 90° relative to the direction in which the diapers 50 are conveyed by the first conveyor belt assembly 3 (i.e., the direction X1).

The turning-round apparatuses 1A, 1B, 1C according to the present invention are applicable not only to turn round the pull-on diaper 50 but also to turn round the other wearing articles such as pull-on diaper covers and open-type diapers having front and rear waist regions adapted to be connected with each other immediately before put on a wearer's body. In the case of the open-type diapers, each diaper is folded in two along its crotch bottom end zone with the topsheet inside so that the diapers may be transferred in such a folded state from the first conveyor belt assembly 3 onto the load-carrying tables 16a, 16b.

Particularly when the turning-round apparatuses 1A, 1B, 1C are used to turn round the disposable diapers 50, it is not essential for the openings 19 formed through the first and second load-carrying tables 16a, 16b to be distributed so as to be covered with the entire waist region of the diaper 50 so far as these openings 19 are distributed so as to be covered with the domain corresponding to the core 57 of the diaper 50 which has relatively high resistance to the air-permeability.

The article turning-round apparatus according to the present invention is primarily characterized in that rotation of the rotary base causes the first and second load-carrying tables to move along with the peripheral zone of the rotary base and simultaneously causes these first and second load-carrying tables to rotate in the peripheral zone of the rotary base around their own axes approximately by an angle of 90° clockwise or counterclockwise. More specifically, the second load-carrying tables rotate in the peripheral zone of the rotary table around their own axes approximately by an angle of 90° in the direction opposite to the direction in which the first load-carrying tables rotate in the course of traveling from the first station 6 toward the second station 7. In addition, the diapers held on the second load-carrying tables can be turned round approximately by an angle of 90° in the direction opposite to the direction in which the diapers held on the first load-carrying tables are turned round and thereby the orientation of the diapers held on the second load-carrying tables can be shifted, in the second station, approximately by an angle of 180° from the orientation of the diapers held on the first load-carrying tables.

The turning-round apparatus according to the present invention is a construction simplified so that the desired principal function to rotate the second load-carrying tables around their own axes relative to the rotary base can be achieved without making the apparatus bulky and complex. Furthermore, it is possible for the apparatus to turn round the articles at a high velocity and thereby to turn round a large number of the articles per a predetermined time.

The apparatus allows also the position of the second station relative to the first station to be freely set by changing the rotational velocity ratio between the pulleys. In other words, there is no restriction so far as the positions on the rotary base at which the articles are loaded and unloaded, respectively, are concerned and a free layout of the apparatus is ensured.

In this turning-round apparatus, the first and second load-carrying tables include the first suction mechanism functioning to suck and hold the articles so that, in the first station, the articles can be smoothly transferred from the first conveyor belt assembly onto these load-carrying tables. In addition, the articles are reliably held on these load-carrying tables under the suction effect of the first suction mechanism without any possibility that the articles might be driven off from the rotary base due to a centrifugal force generated as the rotary base rotates.

With the turning-round apparatus in which the first conveyor belt assembly includes the second suction mechanism functioning to suck and hold the articles thereon, the first conveyor belt assembly can reliably hold the articles thereon under the suction effect until the articles conveyed to the first station on the rotary base. With the turning-round apparatus in which the second conveyor belt assembly includes the third suction mechanism functioning to suck and hold the articles, the second conveyor belt assembly can reliably hold the articles thereon under the suction effect and the articles are smoothly transferred, at the second station, to the second conveyor belt assembly.

The invention claimed is:

1. An article turning apparatus, comprising:
   first and second stations at which a plurality of articles are to be successively loaded and unloaded, respectively;
   a rotary base rotatable about a stationary shaft, said first and second stations being positioned in a peripheral zone of said rotary base; and
   a plurality of load-carrying tables arranged at regular intervals along said peripheral zone, said load-carrying tables being adapted to carry thereon said articles and including first and second load-carrying tables rotatably mounted on said rotary base so as to be rotated around their own axes while moving along with said peripheral zone as said rotary base rotates;
   wherein
   said first and second load-carrying tables are alternatingly arranged on said rotary base so that each of said second load-carrying tables is interposed between one pair of said first load-carrying tables;
   said first and second load-carrying tables are rotated around their own axes in opposite directions while being moved by said rotary base from said first station to said second station as said rotary base rotates; and
   said apparatus further comprises
   first and second belts trained around a portion of said stationary shaft and a portion of said first and second load-carrying tables, respectively, wherein a rotational movement of said rotary base about the portion of said stationary shaft causes said first and second belts to travel about said stationary shaft which belts, in turn, will cause said first and second load-carrying tables, respectively, to rotate about their own axes in the opposite directions;
   a suction box common to all said load-carrying tables; and
   a motor for rotating said rotary base;
   each of said load-carrying tables comprising a plurality of through holes which are in fluid communication with said suction box only when said load-carrying table travels from said first station toward said second station.

2. The apparatus according to claim 1, wherein said suction box includes an elongated opening extending along a path on which said load-carrying tables travel from said first station to said second station.

3. The apparatus according to claim 2, further comprising, for each of said load-carrying tables, a hollow shaft which is attached to said load-carrying table, is rotatably supported by said rotary base and has opposite upper and lower open ends, wherein said load-carrying table has a plurality of through holes in fluid communication with the upper open end of said hollow shaft, the lower open end of said hollow shaft being in fluid communication with said elongated opening of said suction box only when said load-carrying table is on said path.

4. The apparatus according to claim 3, further comprising
   on each of the hollow shafts of said first load-carrying tables, a pulley around which said belt is trained;
   on each of the hollow shafts of said second load-carrying tables, a pulley around which another belt is trained, said another belt is also trained around said portion of the stationary shaft.

5. The apparatus according to claim 2, wherein said elongated opening has a first and second ends located at the first and second stations, respectively, an inner cross section of said elongated opening at said first end is larger than at said second end, thereby inducing different suction forces at said first and second ends and facilitating transfer of said articles at said first and second stations.

6. The apparatus according to claim 1, wherein the through holes of a maximum of two said load-carrying tables are in fluid communication with said suction box at a time.

* * * * *